US007985581B2

(12) United States Patent
Pachuk et al.

(10) Patent No.: US 7,985,581 B2
(45) Date of Patent: Jul. 26, 2011

(54) MULTIPLE RNA POLYMERASE III PROMOTER EXPRESSION CONSTRUCTS

(75) Inventors: Catherine J. Pachuk, Blue Bill, PA (US); Daniel E. McCallus, Oaks, PA (US); Chandrasekhar Satishchandran, Lansdale, PA (US); Martin D. Sigg, Jr., Philadelphia, PA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 491 days.

(21) Appl. No.: 11/660,937

(22) PCT Filed: Aug. 23, 2005

(86) PCT No.: PCT/US2005/029976
§ 371 (c)(1),
(2), (4) Date: Mar. 9, 2009

(87) PCT Pub. No.: WO2006/033756
PCT Pub. Date: Mar. 30, 2006

(65) Prior Publication Data
US 2009/0298909 A1 Dec. 3, 2009

Related U.S. Application Data

(60) Provisional application No. 60/603,622, filed on Aug. 23, 2004, provisional application No. 60/629,942, filed on Nov. 22, 2004.

(51) Int. Cl.
*C07H 21/02* (2006.01)
*C07H 21/04* (2006.01)
*A61K 31/70* (2006.01)
*C12Q 1/68* (2006.01)
*C12N 5/00* (2006.01)

(52) U.S. Cl. ....... 435/320.1; 435/6; 536/23.1; 536/24.1; 536/24.5; 514/44 A

(58) Field of Classification Search .................. None
See application file for complete search history.

(56) References Cited

U.S. PATENT DOCUMENTS

| 5,547,862 | A | 8/1996 | Meador et al. |
| 5,874,242 | A | 2/1999 | Mensa-Wilmot |
| 6,117,651 | A | 9/2000 | Schultz et al. |
| 6,472,171 | B1 | 10/2002 | Toman et al. |
| 6,506,559 | B1 | 1/2003 | Fire et al. |
| 2004/0152117 | A1 | 8/2004 | Giordano et al. |

FOREIGN PATENT DOCUMENTS

| WO | 99/32619 | 7/1999 |
| WO | 00/63364 | 10/2000 |
| WO | 2004/035765 | 4/2004 |
| WO | WO 2005/035718 A2 | 4/2005 |
| WO | WO 2005/111219 A1 | 11/2005 |

OTHER PUBLICATIONS

Bai, F., et al., "Use of RNA interference to prevent lethal murine West Nile Virus infection" The Journal of Infectious Diseases, vol. 191, Apr. 1, 2005, pp. 1148-1154.

Boden, D., et al., "Promoter choice affects the potency of HIV-1 specific RNA interference" Nucleic Acids Research, vol. 31, No. 7, 2003, pp. 5033-5038.

Butz, K., et al., "siRNA targeting of the viral E6 oncogene efficiently kills human papillomavirus-positive cancer cells" Oncogene, vol. 22, 2003, pp. 6938-5945.

Czauderna, F., et al., "Inducible shRNA expression for application in a prostate cancer mouse model" Nucleic Acids Research, vol. 31, No. 21, 2003, p. e127.

Database EMBL-EBI Human 7SK45 DNA, May 20, 1992, Murphy S. et al., "7SK RNA; Alu repetitive sequence; small cytoplasmic RNA" Database accession No. XO4992.

Giladi, H., et al., "Small interfering RNA inhibits Hepatitis B virus replication in mice" Molecular Therapy, Academic Press, San Diego, CA, US, vol. 8, No. 5. 2003, pp. 769-776.

Jiang, M. and Milner J.,"Selective silencing of viral gene expression in HPV-positive human cervical carcinoma cells treated with siRNA, a primer of RNA interference" Oncogene, vol. 21, 2002, pp. 6041-6048.

Jiang, M., et al., "Gel-based application of siRNA to human epithelial cancer cells induces RNAI-dependent apoptosis" Oligonucleotides, vol. 14, 2004, pp. 239-248.

Krönk, J., et al., "Alternative approaches for efficient inhibition of Hepatitis C virus RNA replication by small interfering RNAs" Journal of Virology, vol. 78, No. 7, Apr. 2004, pp. 3436-3446.

Li, M.J., et al., "Inhibition of HIV-1 infection by lentiviral vectors expressing Pol III-promoted anti-HIV RNAs" Molecular Therapy, vol. 8, No. 2, Aug. 2003, pp. 196-206.

McCaffrey, A.P., et al., "Inhibition of hepatitis B virus in mice by RNA interference" Nature Biotechnology, vol. 21, No. 6, 2003, pp. 639-644.

Milner ,J., "RNA interference for treating cancers caused by viral infection" Expert Opinion on Biological Therapy, vol. 3, No. 3, 2003, pp. 459-467.

Murphy, S., et al., "A sequence upstream from the coding region is required for the transcription of the 7SK RNA genes" Nucleic Acids Research, vol. 14, No. 23, 1986,. pp. 9243-9260.

Pebernard, S. and Iggo, R.D., "Determinants of interferon-stimulated gene induction by RNAi vectors" Differentiation, vol. 72, Mar. 2004, pp. 103-111.

Tallet-Lopez, B., et al., "Antisense oligonucleotides targeted to the domain IIId of the hepatitis C virus IRES compete with 40S ribosomal subunit binding and prevent in vitro translation" Nucleic Acids Research, vol. 31, No. 2, 2003, pp. 734-742.

Ying Chen, et al., "Inhibition of hepatitis B virus replication by stably expressed shRNA" Biochemical & Biophysical Research Communications, vol. 311, 2003, pp. 398-404.

(Continued)

*Primary Examiner* — Sean McGarry
(74) *Attorney, Agent, or Firm* — Nixon Peabody LLP; Mark J. FitzGerald

(57) ABSTRACT

Expression constructs comprising at least two different RNA polymerase III promoters, wherein each promoter is operably linked to a nucleic acid sequence encoding an RNA effector molecule, are disclosed herein. Further provided are expression constructs comprising multiple polymerase III promoters operably linked to sequences encoding short hairpin RNA molecules, which may comprise single and/or multiple fingers. The provided constructs are useful for in vivo delivery of RNA molecules effective in gene silencing, including of viral genes including HBV and HCV.

62 Claims, 18 Drawing Sheets

OTHER PUBLICATIONS

Yoshinouchi, M., et al., "In vitro and in viva growth suppression of human Papillomavirus 16-positive cervical cancer cells by E6 siRNA" Molecular Therapy, vol. 8, No. 5, Nov. 2003, pp. 782-768.
Database Embase, May 2005, Zeitlin et al., "Avian influenza." XP002567099 Database accession No. EMB-2005231319 & Current Infectious Disease Reports, 7(3):193-199 (2005).
Gewin et al., Genes & Development, 18(18):2269-2282 (2004). "Identification of a novel telomerase repressor that interacts with the human papillomavirus type-16 E6/E6-AP complex."
Lee et al., Nat Biotechnol, 20:500-05 (2002).
Miyagishi and Taira, Nat Biotechnol, 20:497-500 (2002).
Trinh et al., Focus, 16:78-80 (1994).
Yu et al., Proc Natl Acad Sci USA, 99:6047-52 (2002).

FIG 1
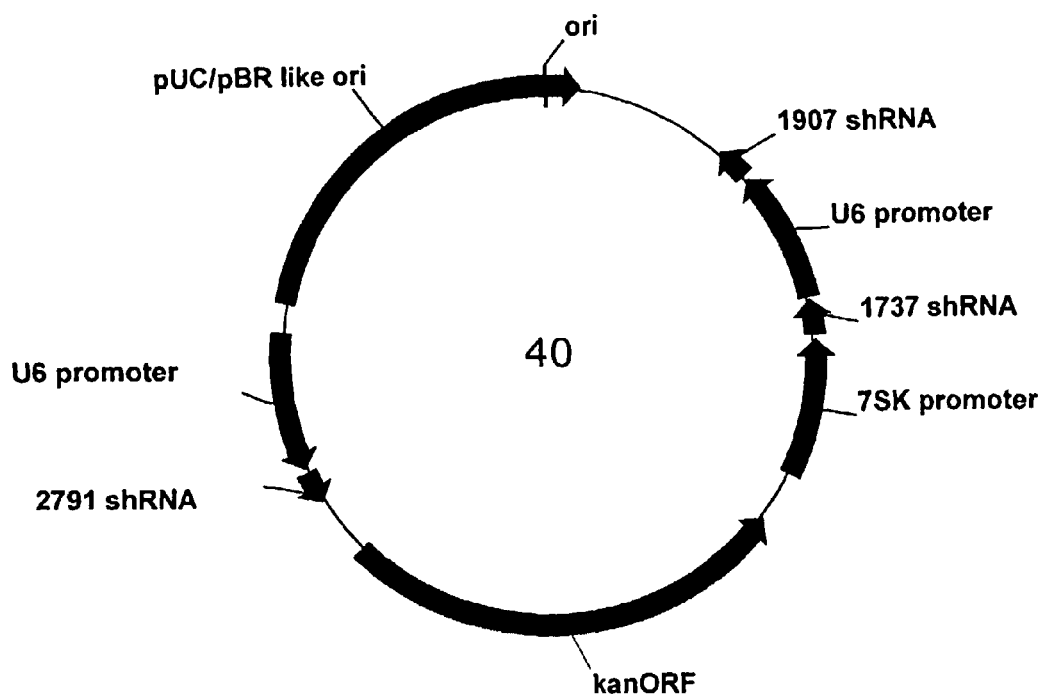
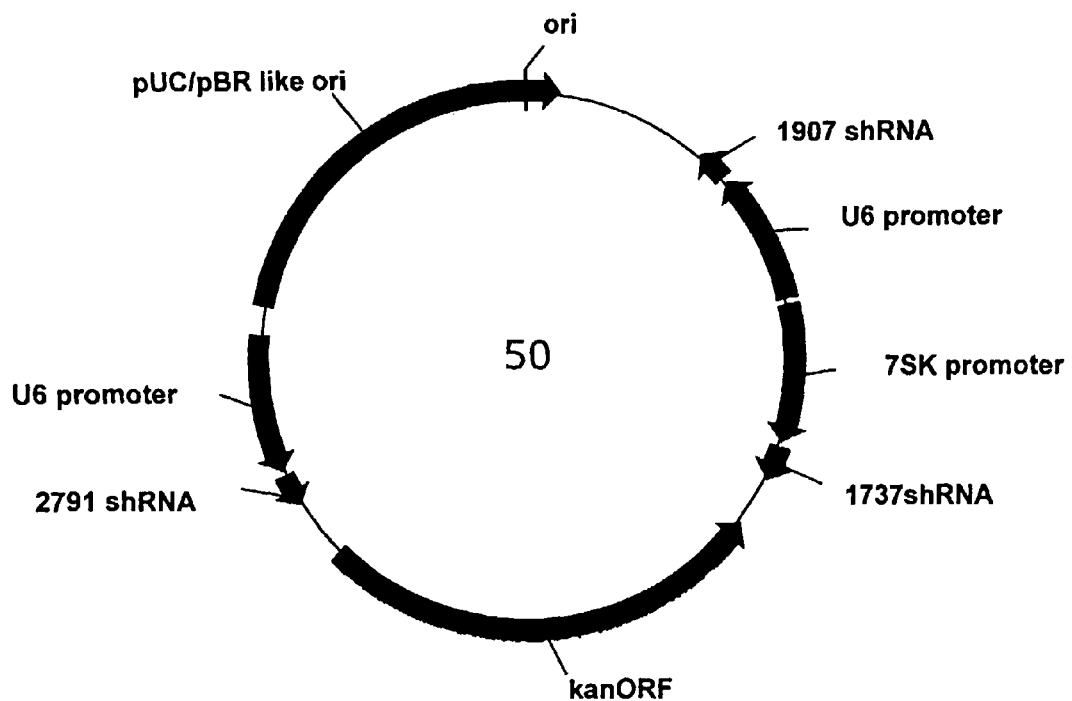

FIG 2
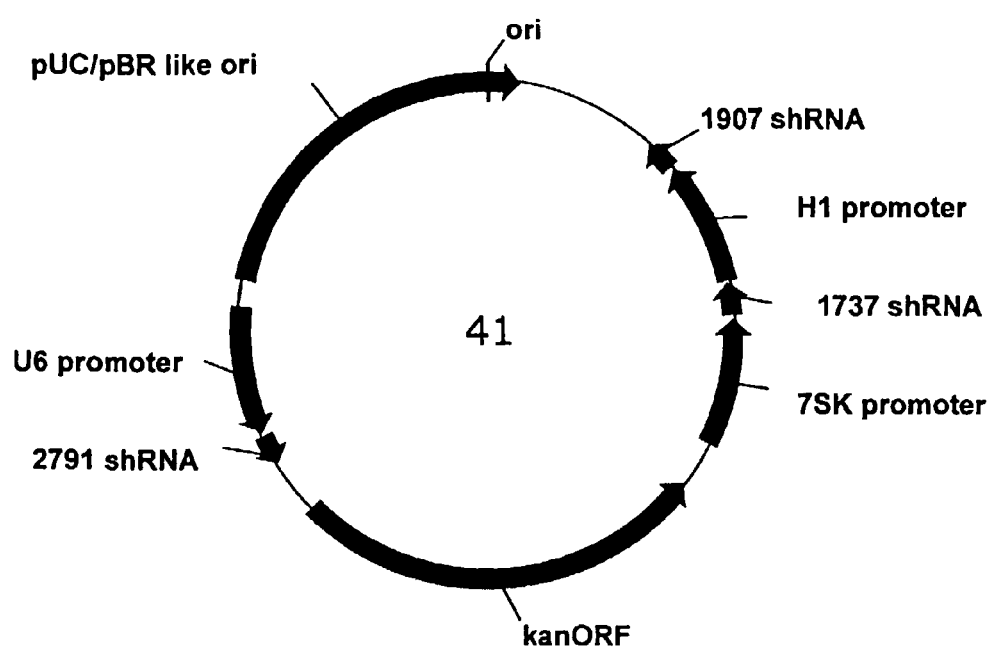
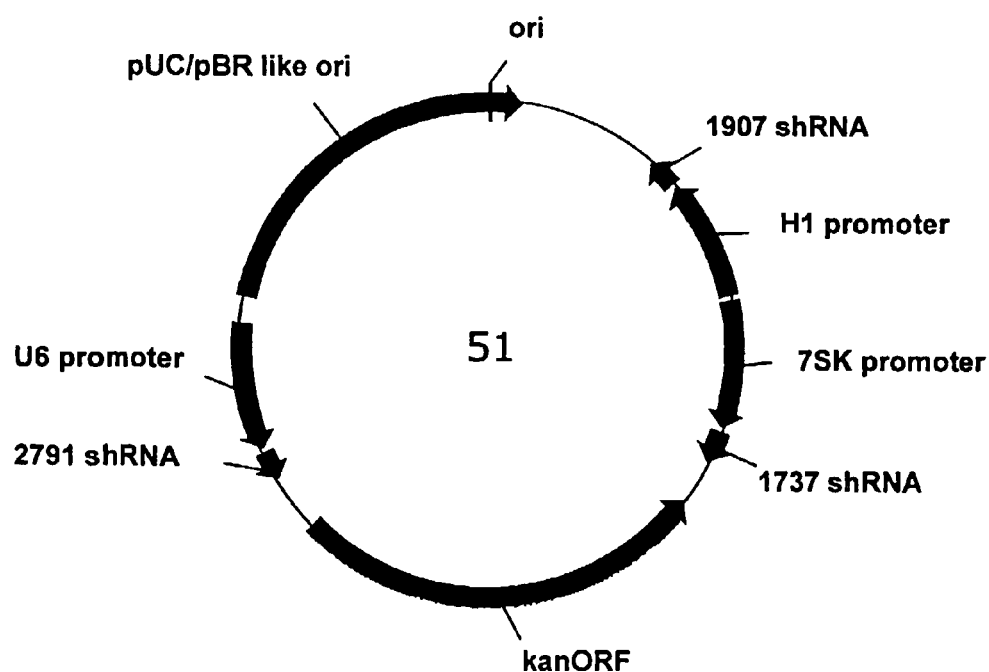

FIG 3

| eiRNA vector | fusion target | luc activity |
|---:|:---|---:|
| 40 | Luc | 91.7 |
| 40 | Luc-2791 | 67.3 |
| 40 | Luc-1907 | 18.4 |
| 40 | Luc-1737 | 90.5 |
| 40 | Luc-ayw | 44.6 |
| 50 | Luc | 155.4 |
| 50 | Luc-2791 | 104 |
| 50 | Luc-1907 | 21 |
| 50 | Luc-1737 | 58.8 |
| 50 | Luc-ayw | 24.5 |
| 41 | Luc | 90 |
| 41 | Luc-2791 | 67.3 |
| 41 | Luc-1907 | 22.2 |
| 41 | Luc-1737 | 47.8 |
| 41 | Luc-ayw | 52 |
| 51 | Luc | 85 |
| 51 | Luc-2791 | 54.1 |
| 51 | Luc-1907 | 29 |
| 51 | Luc-1737 | 133.5 |
| 51 | Luc-ayw | 32.7 |

FIG 4

4a) 7SK promoter
1   ctgcagtatt tagcatgccc cacccatctg caaggcattc tggatagtgt caaaacagcc
61  ggaaatcaag tccgtttatc tcaaacttta gcattttggg aataaatgat atttgctatg
121 ctggttaaat tagatttag ttaaatttcc tgctgaagct ctagtacgat aagcaacttg
181 acctaagtgt aaagttgaga tttccttcag gtttatatag cttgtgcgcc gcctGTCGAC 4b) H1 promoter
250          g agggacaggg gagtggcgcc ctgcaatatt tgcatgtcgc tatgtgttct
301 gggaaatcac cataaacgtg aaatgtcttt ggatttggga atcttataag ttctgtatga
361 gaccactctt tcccaGTCGAC 4c) U6 promoter
 65       aaggtc gggcaggaag agggcctatt tcccatgatt ccttcatatt tgcatatacg
121 atacaaggct gttagagaga taattagaat taatttgact gtaaacacaa agatattagt
181 acaaaatacg tgacgtagaa agtaataatt tcttgggtag tttgcagttt taaaattatg
241 ttttaaaatg gactatcata tgcttaccgt aacttgaaag tatttcgatt tcttggcttt
301 atatatcttg tggaaaggac gaaacaccgG TCGAC 4d) 7SK-e promoter
1   ctgcagtatt tagcatgccc cacccatctg caaggcattc tggatagtgt caaaacagcc
61  ggaaatcaag tccgtttatc tcaaacttta gcattttggg aataaatgat atttgctatg
121 ctggttaaat tagatttag ttaaatttcc tgctgaagct ctagtacgat aagcaacttg
181 acctaagtgt aaagttgaga tttccttcag gtttatatag cttgtgcgcc gcctgggtac
241 ctcgGTCGAC 4e) 7SK-4A promoter
1   ctgcagtatt tagcatgccc cacccatctg caaggcattc tggatagtgt caaaacagcc
61  ggaaatcaag tccgtttatc tcaaacttta gcattttggg aataaatgat atttgctatg
121 ctggttaaat tagatttag ttaaatttcc tgctgaagct ctagtacgat aagcaacttg
181 acctaagtgt aaagttgaga tttccttcag gtttatatag cttgtgcgcc gcctGTCGAC
241 aaaa

FIG 5 shRNA 2791:
AAAACGCCGCAGACACATCCAAGAGAACTTTGGATGTGTCTGCGGCGTTTT shRNA 1907:
TTCCGCAGTATGGATCGGCAGAGAACTTGCCGATCCATACTGCGGAA shRNA 1737:
GGATTCAGCGCCGACGGGACGAGAGAACTTCGTCCCGTCGGCGCTGAATCC shRNA 799:
GCCTCGCAGACGAAGGTCTCAAGAGAACTTTGAGACCTTCGTCTGCGAGGC shRNA 1991:
TGCGTCAGCAAACACTTGGCAAGAGAACTTTGCCAAGTGTTTGCTGACGCA shRNA 1943:
TCCACGCATGCGCTGATGGCCAGAGAACTTGGCCATCAGCGCATGCGTGGA

FIG 6

| construct | input (ng) | %inhibition |
|---:|---:|---:|
| 40 | 1 | 34.2 |
| 40 | 5 | 49.4 |
| 40 | 10 | 78.9 |
| 40 | 25 | 93.3 |
| 40 | 50 | 97 |
| 50 | 1 | 41.2 |
| 50 | 5 | 62.7 |
| 50 | 10 | 80.6 |
| 50 | 25 | 91.8 |
| 50 | 50 | 97.1 |

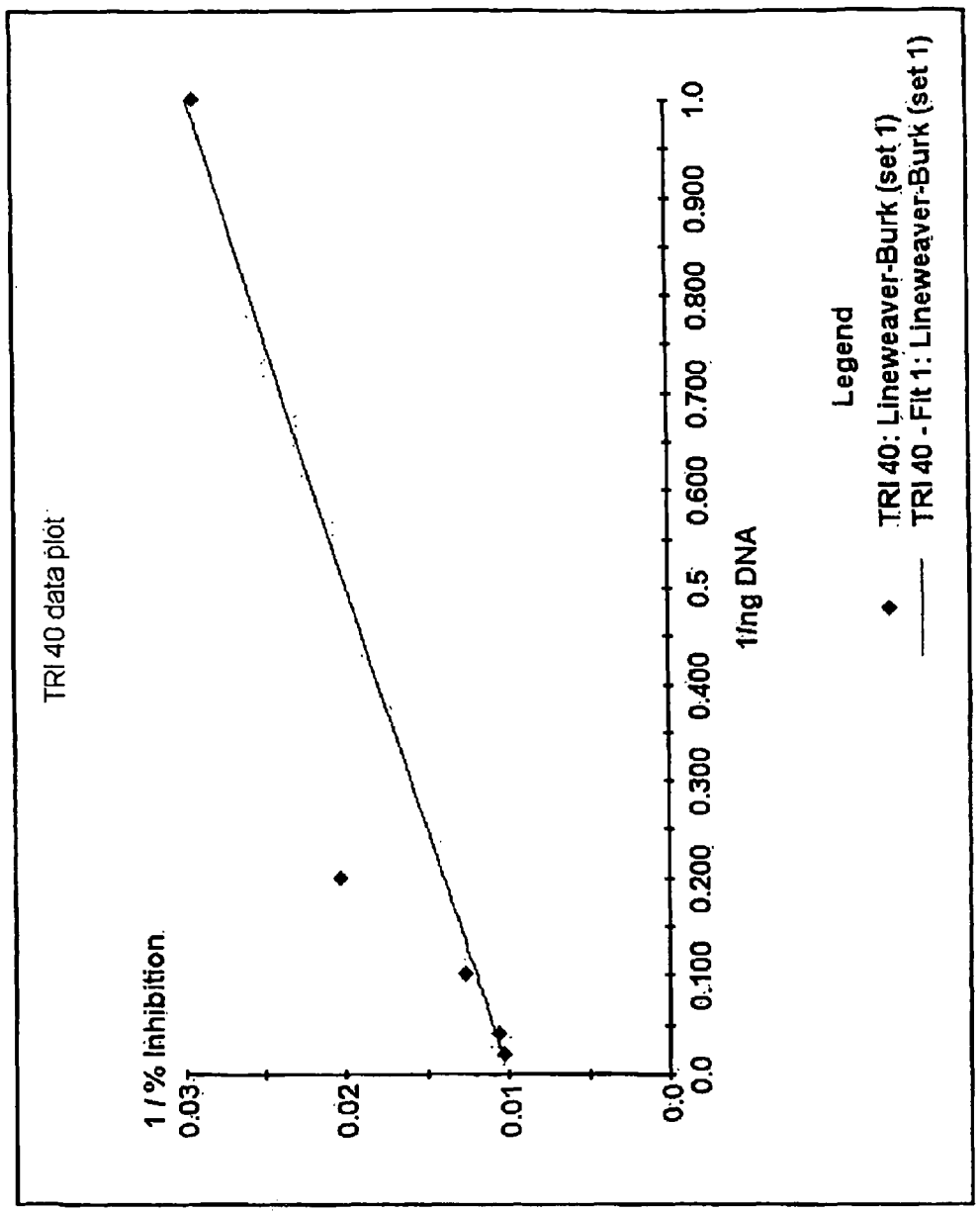

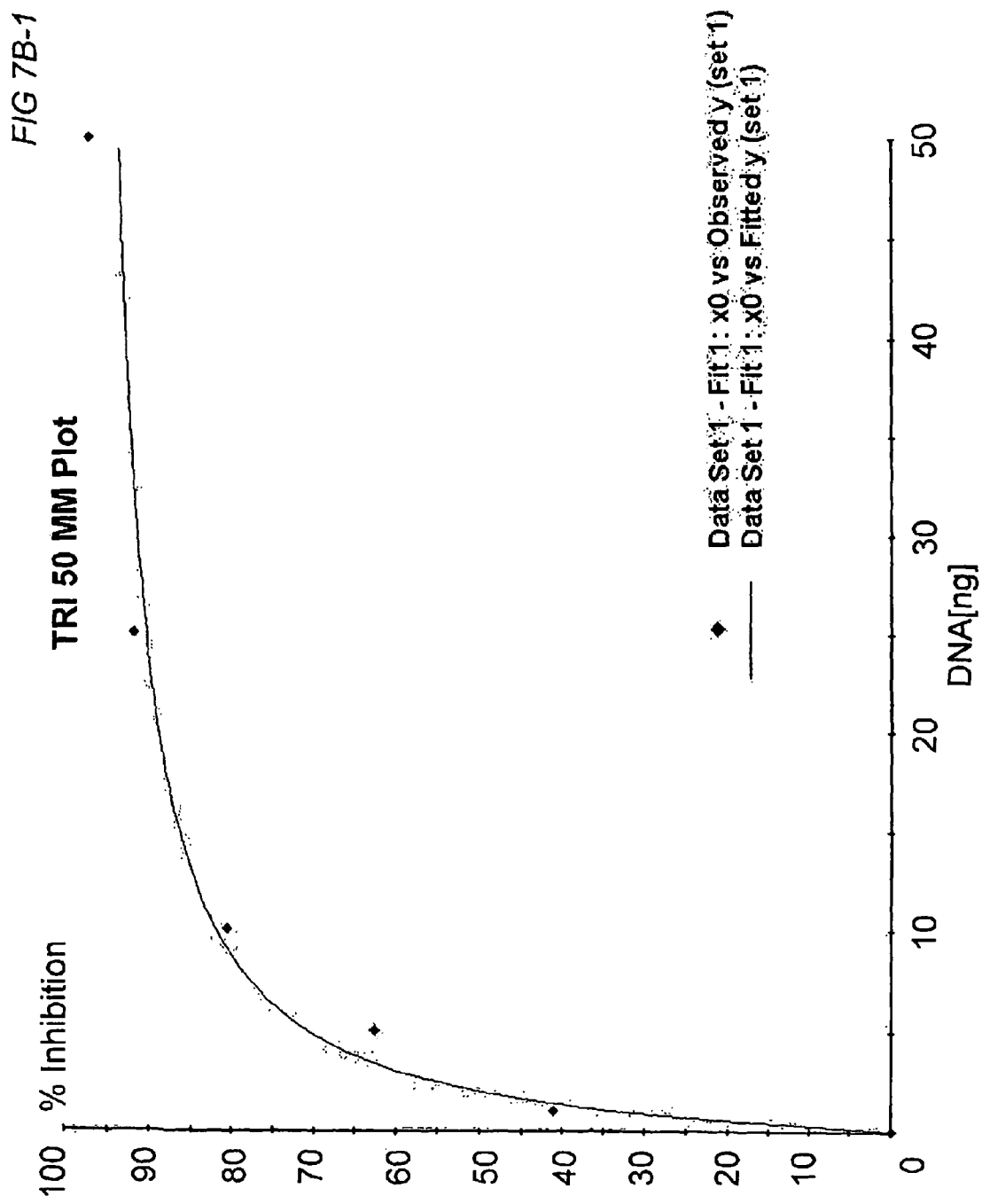

FIG 10

| TARGET CONSTRUCTS | QUAD EXP 1 | QUAD EXP 2 | QUAD EXP 3 | 1737 ONLY | 1907 ONLY | 2791 ONLY | 799 ONLY |
|---|---|---|---|---|---|---|---|
| LUC ONLY | 108.95 | 96.44 | 106.70 | 117.97 | 77.08 | 128.93 | 99.36 |
| LUC + HBV GENOME | 38.10 | 40.88 | 34.75 | 55.08 | 45.43 | 20.72 | 67.52 |
| LUC + HBV TARGET 1737 | 39.84 | 45.38 | 38.71 | 39.95 | | | |
| LUC + HBV TARGET 1907 | 66.28 | 65.80 | 65.80 | | 27.77 | | |
| LUC + HBV TARGET 2791 | 39.99 | 32.38 | 33.35 | | | 8.00 | |
| LUC + HBV TARGET 799 | 19.27 | 19.98 | 17.57 | | | | 14.28 | shRNA VECTORS

Fig 11

| shRNA | Promoter | sAg IC50 | eAg IC50 |
|---|---|---|---|
| 1737 | U6 | 24.06 | 50.91 |
| 1737 | 7SK | 26.95 | n.d. |
| 1737 | 7SK4a | 0.54 | 1.14 |
| 1943 | U6 | 17.87 | 12.93 |
| 1943 | 7SK | 19.45 | 59.64 |
| 1943 | 7SK4a | 0.76 | 0.67 |
| 799 | U6 | n.d | 15.07 |
| 799 | 7SK | n.d | 14.38 |
| 799 | 7SK4a | n.d | 0.59 |

FIG 12

| Pol III Promoters | shRNA | IC50 sAg (ng/ml) | IC50 eAg (ng/ml) |
|---|---|---|---|
| 1 [U6] | #1907 | 4.3 | 11.06 |
| 2 [U6 7SK] | #1907, #1737 | 1.4 | n.d. |
| 3 [U6 7SK* 7SK] | #1907, #1737, #2791 | 0.46 | 0.39 |
| 4 [U6 7SK* 7SK* 7SK] | #1907, #1737, #2791, #799 | 0.36 | 0.31 |

FIG 13
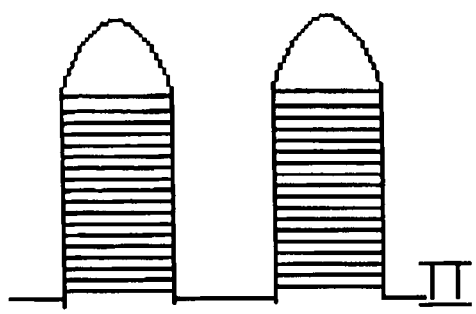
U6_1737-N16-2791
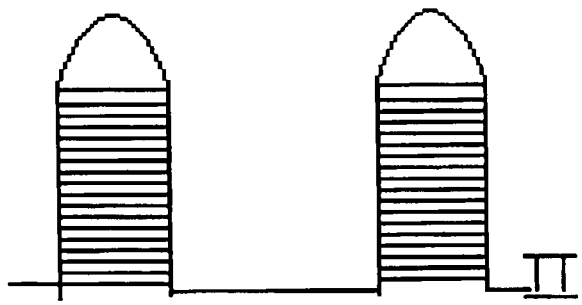
U6_1737-N42-2791
| Reporter Construct | U6_1737-N16-2791 | U6_1737-N42-2791 |
|---|---|---|
| LUC | 100.00 | 100.00 |
| LUC-HBV Genome | 19.46 | 26.16 |
| LUC-1737 Target | 51.52 | 38.62 |
| LUC-2791 Target | 14.55 | 23.75 |

SEQUENCE LISTING

```
<160> NUMBER OF SEQ ID NOS: 12

<210> SEQ ID NO 1
<211> LENGTH: 240
<212> TYPE: DNA
<213> ORGANISM: Artificial
<220> FEATURE:
<223> OTHER INFORMATION: Homo sapiens 7SK promoter, GenBank Accession
      No. X04992, bases 1-234, with a Sal I restriction site at bases
      235-240

<400> SEQUENCE: 1
ctgcagtatt tagcatgccc cacccatctg caaggcattc tggatagtgt caaaacagcc      60
ggaaatcaag tccgtttatc tcaaacttta gcattttggg aataaatgat atttgctatg     120
ctggttaaat tagattttag ttaaatttcc tgctgaagct ctagtacgat aagcaacttg     180
acctaagtgt aaagttgaga tttccttcag gtttatatag cttgtgcgcc gcctgtcgac     240

<210> SEQ ID NO 2
<211> LENGTH: 132
<212> TYPE: DNA
<213> ORGANISM: Artificial
<220> FEATURE:
<223> OTHER INFORMATION: Homo sapiens H1 promoter, GenBank Accession
```

No. X16612, bases 250-375, with a Sal I restriction site at
bases 376-381

<400> SEQUENCE: 2

```
gagggacagg ggagtggcgc cctgcaatat ttgcatgtcg ctatgtgttc tgggaaatca    60
ccataaacgt gaaatgtctt tggatttggg aatcttataa gttctgtatg agaccactct   120
ttcccagtcg ac                                                      132
```

<210> SEQ ID NO 3
<211> LENGTH: 271
<212> TYPE: DNA
<213> ORGANISM: Artificial
<220> FEATURE:
<223> OTHER INFORMATION: Homo sapiens U6 promoter, GenBank Accession
      No. M14486, bases 65-329, with a Sal I restriction site at bases
      330-335

<400> SEQUENCE: 3

```
aaggtcgggc aggaagaggg cctatttccc atgattcctt catatttgca tatacgatac    60
aaggctgtta gagagataat tagaattaat ttgactgtaa acacaaagat attagtacaa   120
aatacgtgac gtagaaagta ataatttctt gggtagtttg cagttttaaa attatgtttt   180
aaaatggact atcatatgct taccgtaact tgaaagtatt tcgatttctt ggctttatat   240
atcttgtgga aaggacgaaa caccggtcga c                                 271
```

<210> SEQ ID NO 4
<211> LENGTH: 250
<212> TYPE: DNA
<213> ORGANISM: Artificial
<220> FEATURE:
<223> OTHER INFORMATION: Homo sapiens 7SK promoter, GenBank Accession
      No. X04992, bases 1-244, with a Sal I restriction site at bases
      245-250

<400> SEQUENCE: 4

```
ctgcagtatt tagcatgccc cacccatctg caaggcattc tggatagtgt caaaacagcc    60
ggaaatcaag tccgtttatc tcaaacttta gcattttggg aataaatgat atttgctatg   120
ctggttaaat tagattttag ttaaatttcc tgctgaagct ctagtacgat aagcaacttg   180
acctaagtgt aaagttgaga tttccttcag gtttatatag cttgtgcgcc gcctgggtac   240
ctcggtcgac                                                         250
```

<210> SEQ ID NO 5
<211> LENGTH: 244
<212> TYPE: DNA
<213> ORGANISM: Artificial
<220> FEATURE:
<223> OTHER INFORMATION: Homo sapiens 7SK-4A promoter, GenBank
      Accession No. X04992, bases 1-234, with a Sal I restriction site
      at bases 235-240 followed by 4 A residues

<400> SEQUENCE: 5

```
ctgcagtatt tagcatgccc cacccatctg caaggcattc tggatagtgt caaaacagcc    60
ggaaatcaag tccgtttatc tcaaacttta gcattttggg aataaatgat atttgctatg   120
ctggttaaat tagattttag ttaaatttcc tgctgaagct ctagtacgat aagcaacttg   180
acctaagtgt aaagttgaga tttccttcag gtttatatag cttgtgcgcc gcctgtcgac   240
aaaa                                                               244
```

<210> SEQ ID NO 6
<211> LENGTH: 51

-continued

```
<212> TYPE: DNA
<213> ORGANISM: Artificial
<220> FEATURE:
<223> OTHER INFORMATION: HepB based shRNA 2791

<400> SEQUENCE: 6
aaaacgccgc agacacatcc aagagaactt tggatgtgtc tgcggcgttt t          51

<210> SEQ ID NO 7
<211> LENGTH: 47
<212> TYPE: DNA
<213> ORGANISM: Artificial
<220> FEATURE:
<223> OTHER INFORMATION: HepB based shRNA 1907

<400> SEQUENCE: 7
ttccgcagta tggatcggca gagaacttgc cgatccatac tgcggaa              47

<210> SEQ ID NO 8
<211> LENGTH: 51
<212> TYPE: DNA
<213> ORGANISM: Artificial
<220> FEATURE:
<223> OTHER INFORMATION: HepB based shRNA 1737

<400> SEQUENCE: 8
ggattcagcg ccgacgggac gagagaactt cgtcccgtcg gcgctgaatc c          51

<210> SEQ ID NO 9
<211> LENGTH: 51
<212> TYPE: DNA
<213> ORGANISM: Artificial
<220> FEATURE:
<223> OTHER INFORMATION: HepB based shRNA 799

<400> SEQUENCE: 9
gcctcgcaga cgaaggtctc aagagaactt tgagaccttc gtctgcgagg c          51

<210> SEQ ID NO 10
<211> LENGTH: 51
<212> TYPE: DNA
<213> ORGANISM: Artificial
<220> FEATURE:
<223> OTHER INFORMATION: HepB based shRNA 1991

<400> SEQUENCE: 10
tgcgtcagca aacacttggc aagagaactt tgccaagtgt ttgctgacgc a          51

<210> SEQ ID NO 11
<211> LENGTH: 51
<212> TYPE: DNA
<213> ORGANISM: Artificial
<220> FEATURE:
<223> OTHER INFORMATION: HepB based shRNA 1943

<400> SEQUENCE: 11
tccacgcatg cgctgatggc cagagaactt ggccatcagc gcatgcgtgg a          51

<210> SEQ ID NO 12
<211> LENGTH: 10
<212> TYPE: DNA
<213> ORGANISM: Artificial
<220> FEATURE:
<223> OTHER INFORMATION: Promoter 7SK4a
```

```
<400> SEQUENCE: 12
gtcgacaaaa                                                                10
```

MULTIPLE RNA POLYMERASE III PROMOTER EXPRESSION CONSTRUCTS

CROSS-REFERENCE TO RELATED APPLICATIONS

This application claims the benefit of U.S. Provisional Application No. 60/603,622, filed Aug. 23, 2004, and U.S. Provisional Application No. 60/629,942, filed Nov. 22, 2004, each of which is incorporated by reference herein in their entireties.

DESCRIPTION OF THE TEXT FILE SUBMITTED ELECTRONICALLY

The contents of the text file submitted electronically are incorporated herein by reference in their entirety: A computer readable format copy of the Sequence Listing (filename: NUCL00802US2ndSubSeqList.txt, date recorded: Jun. 4, 2009, file size 5 kilobytes).

FIELD OF THE INVENTION

The general field of this invention is the method of use and composition of novel recombinant DNA molecules with the ability to efficiently direct (within a cell, tissue or organism) the abundant production of small, engineered RNA molecules which are useful for the inhibition of genes involved in disease or abnormal cellular function. In particular, this invention provides the means for simultaneous production of multiple (2, 3, 4, 5 or more) distinct small RNA molecules from a single recombinant DNA molecule using a design appropriate for human therapeutic applications.

BACKGROUND OF THE INVENTION

Recently, the phenomenon of RNAi or double-stranded RNA (dsRNA)-mediated gene silencing has been recognized, whereby dsRNA complementary to a region of a target gene in a cell or organism inhibits expression of the target gene (see, e.g., WO 99/32619, published 1 Jul. 1999, Fire et al.; U.S. Pat. No. 6,506,559: "Genetic Inhibition by Double-Stranded RNA;" WO 00/63364: "Methods and Compositions for Inhibiting the Function of Polynucleotide Sequences," Pachuk and Satishchandran; and U.S. Provisional Application Ser. No. 60/419,532, filed Oct. 18, 2002 (WO2004/035765, published 29 Apr. 2004: "Double-Stranded RNA Structures and Constructs, and Methods for Generating and Using the Same"). Double-stranded RNA (dsRNA) gene silencing presents a particularly exciting potential application for nucleic acid-based technology. Double-stranded RNA has been shown to induce gene silencing in a number of different organisms. Gene silencing can occur through various mechanisms, one of which is post-transcriptional gene silencing (PTGS). In post-transcriptional gene silencing, transcription of the target locus is not affected, but the RNA half-life is decreased. Exogenous dsRNA has been shown to act as a potent inducer of PTGS in plants and animals, including nematodes, trypanosomes, insects, and mammals. Transcriptional gene silencing (TGS) is another mechanism by which gene expression can be regulated. In TGS, transcription of a gene is inhibited. In PTGS, the cytoplasmic compartment of the cell is the location of the machinery of the silencing complex. In TGS, the effector dsRNA is ostensibly active in the nuclear compartment of the cell. The potential to harness dsRNA mediated gene silencing for research, therapeutic, and prophylactic indications is enormous. The exquisite sequence specificity of target mRNA degradation and the systemic properties associated with PTGS make this phenomenon ideal for functional genomics and drug development.

Some current methods for using dsRNA in vertebrate cells to silence genes result in undesirable non-specific cytotoxicity or cell death due to dsRNA-mediated stress responses, including the interferon response. Early reports stated categorically that dsRNA-mediated toxicity in vertebrates is associated only with dsRNAs greater than 30 bps in length, not with siRNAs (short synthetic duplex dsRNA molecules of 21-23 bp) or other duplex dsRNAs of less than 30 bps. Despite the early acceptance of this dogma, more recent reports are establishing that non-specific silencing effects and other toxicity, including induction of cellular stress response pathways such as the interferon response, also occur with exogenously introduced siRNA molecules. Applicants, however, have demonstrated that intracellular expression of dsRNA molecules from a nucleic acid expression construct, including the long dsRNAs reported to induce toxicity in vertebrate cells, can be accomplished under conditions which do not trigger dsRNA-mediated toxicity. See, e.g., Published U.S. Patent Application No. 2004/0152117, Satishchandran, Pachuk, and Giordano. Accordingly, both long and short dsRNA molecules, including dsRNA hairpin molecules, can be used in mammals and other vertebrates without inducing an interferon or other dsRNA-mediated stress response, if the dsRNA molecules are expressed within the host cell rather than introduced exogenously into the cell. However, a challenge remains in that the practical implementation of such dsRNA methods requires the efficient intracellular production and delivery of dsRNA molecules from dsRNA expression constructs.

For RNAi applications as well as use of nucleic acids for other mechanisms of biological activity, it is frequently desirable to express a biologically active nucleic acid intracellularly from a nucleic acid expression construct. The effectiveness of such methods depends upon an ability to efficiently express the selected nucleic acid in the target host cell in a therapeutically relevant manner, e.g., in a biologically active, non-toxic form to the desired target cell or cells in vivo or in vitro, in effective amounts and duration in the desired subcellular location or location(s). This presents a particular challenge in cells which are difficult to transfect, e.g., primary cells, certain cell lines, e.g., K5625, a human leukemia cell line, and for in vivo applications. Thus, improved expression systems, expression constructs and methods are needed for intracellular expression of nucleic acids from nucleic acid expression constructs in eukaryotes. Desirably, these methods may be used to provide nucleic acids capable of achieving any of their varied biological functions, including production of a desired polypeptide and/or a desired RNA effector molecule, e.g., a ribozyme, antisense, triplex-forming, and/or dsRNA in in vitro samples, cell culture, and intact animals (e.g., vertebrates, such as mammals, including humans).

In the decades since the advent of biotechnology, a huge variety of vectors, expression constructs, and expression systems, including circular plasmids, linearized plasmids, cosmids, viral genomes, recombinant viral genomes, artificial chromosomes, etc., have been developed for use in prokaryotes and/or eukaryotes. Use of these expression systems in bacterial cell culture has made such recombinant proteins as interferon (alpha), interferon (beta), erythropoietin, factor VIII, human insulin, t-PA, and human growth hormone a standard part of the pharmaceutical armamentarium.

Among the tremendous variety of expression vectors and expression systems that have been developed in the field of biotechnology and molecular biology are expression systems containing multiple promoters on the same vector. One such type of multiple promoter expression system utilizes vectors containing multiple promoters (i.e., two or more promoters) that are active in a prokaryote or in the same subcellular compartment of a eukaryotic cell. For example, such multiple promoter systems in the art have been developed to permit expression of more than one sequence in the same compartment of the same cell (e.g., two distinct sequences or a sense and antisense sequence designed to form a dsRNA), or they may be used to express the same sequence within different cells or organisms (e.g., a prokaryote and a eukaryote) or to obtain more efficient transcription of a single operably linked sequence. Frequently seen are, e.g., multiple RNA polymerase II promoters or bacteriophage promoters on the same plasmid, such as, e.g., two polymerase II promoters-such as CMV and SV40, or a bacteriophage T7 promoter and a bacteriophage SP6 promoter.

Further, such multiple promoters can be arranged within the vector in any number of orientations and configurations. For example, two promoters can direct transcription both from the same or from the opposite strands of the vector. If oriented on the same strand, they drive transcription in the same direction within the vector. Alternatively, multiple promoters may be encoded on opposite strands and arranged either convergently or divergently with respect to each other in the same vector, in which case, transcription proceeds in opposite directions within the vector. Further, a variety of terms have been developed in the art to describe the relative position of multiple promoters within a single vector. The term "tandem" has been used to describe multiple promoters that all reside on, and are all operably linked to, the 5' end of the sequence to be transcribed. Tandem promoters can be the same or different promoters. The term "flanking" promoters describes the orientation of multiple promoters in which the sequence to be transcribed is flanked on both the 5' and the 3' end by a promoter in such a manner that each promoter, when transcriptionally active, is capable of transcribing one strand of the sequence to be transcribed. The flanking promoters can be the same or different promoters. E.g., a set of bacteriophage T7 RNA polymerase promoters flanking the 5' and 3' ends of a sequence is a common method for expressing separate sense and antisense strands to form duplex dsRNA (WO99/32619, Fire et al., published Jul. 1, 1999).

Multiple tandem promoters are described, e.g., in U.S. Pat. No. 5,547,862, which discloses a DNA vector which comprises an RNA transcription sequence positioned downstream from two or more tandem promoters which are recognized by distinct RNA polymerases and are each capable of promoting expression of the RNA transcription sequence.

A method for making mammalian collagen or procollagen in yeast is disclosed in U.S. Pat. No. 6,472,171 using a construct comprising, in opposite orientations, two mammalian collagen genes operably linked to a single or dual, divergent heterologous promoter(s). The promoter(s) driving the two collagen genes may be the same promoter, or different promoters, and may be used to provide for the coordinate, preferably simultaneous, expression of the two collagen genes.

Expression vectors containing dual bacterial promoters arranged in tandem and operably linked to a heterologous nucleic acid encoding a desired polypeptide are disclosed in U.S. Pat. No. 6,117,651. The dual promoter comprises a first component derived from a tac-related promoter (which is itself a combination of the lac and trp promoters) and a second promoter component obtained from a bacterial gene or operon that encodes an enzyme involved in galactose metabolism. The dual bacterial promoter system acts synergistically to provide a high level of transcription of the linked sequence in a prokaryotic cell such as E. coli.

U.S. Pat. No. 5,874,242 discloses a vector which provides for the translation of an inserted coding sequence in both eukaryotic and prokaryotic host cells. Specifically, such vectors include either a bifunctional promoter (functional in both eukaryotes and prokaryotes) or dual promoters (promoters separately functional in eukaryotes and prokaryotes) for efficient expression in both prokaryotic and eukaryotic cells.

There are a myriad of other examples in the art disclosing variations on themes of multiple promoters used in the same vector. However, there remains a need for new classes of expression vectors suitable for expression of multiple small RNA effector molecules, including multiple dsRNA hairpins of various lengths, e.g., shRNAs, bi- and multi-fingered dsRNA hairpins, long dsRNA hairpins, etc.), in a context useful for human therapeutic intervention. It is well-established that vector-directed expression short RNA effector molecules including short hairpin dsRNAs is most efficient when under the control of one of the mammalian promoter types which the cell naturally employs for expression of normally occurring small RNA molecules. These promoters typically comprise the family of RNA Polymerase III promoters. There are further defined in the literature three main subclasses of RNA polymerase III promoters, Type 1, Type 2 and Type 3. Prototypical examples of promoters in each class are found in genes encoding 5s RNA (Type 1), various transfer RNAs (Type 2) and U6 small nuclear RNA (Type 3). Another promoter family (transcribed by RNA Polymerase I) is also dedicated in the cell to transcription of small structural RNAs; however, this family appears to be less diverse in sequence than the RNA Polymerase III promoters. Finally, RNA Polymerase II promoters are used in the transcription of the protein-coding messenger RNA molecules, as distinguished from the small structural and regulatory RNA mentioned above. The majority of promoter systems known in the art utilize RNA Polymerase II promoters, which are not optimal for production of small RNAs.

RNA polymerase III promoter-based vectors containing one promoter have been described in the art (see, e.g., U.S. Pat. No. 5,624,803, Noonberg et al., "In vivo oligonucleotide generator, and methods of testing the binding affinity of triplex forming oligonucleotides derived therefrom"), and a description of U6-based vector systems can be found in Lee et al., Nat. Biotechnol. 20:500-05 (2002). Yu et al., *Proc. Natl. Acad. Sci. USA* 99:6047-52 (2002), describe an expression system for short duplex siRNAs comprising a T7 and U6 promoter. Miyagishi and Taira, *Nat. Biotechnol.* 20:497-500 (2002), describe expression plasmids for short duplex siRNAs comprising expression cassettes containing tandem U6 promoters, each transcribing either the sense or the antisense strand of an siRNA, which are then annealed to form duplex siRNAs. Also described are expression plasmids including two such U6 based siRNA expression cassettes. The authors state that they utilized duplex siRNA expression cassettes because of their stability compared to stem-loop or hairpin-type dsRNA producing cassettes which include an unstable palindromic sequence.

In order to enable therapeutic utility of short RNA expression vector systems several criteria must be met with regard to structure as well as function. For human use, vectors must be designed to minimize the possibility of recombination events occurring both between vector sequences and genome sequences, and within the vector itself. These events are potentiated by regions of sequence identity (or homology)

between the vector and the cellular genome sequence or between elements within the vector itself. The vectors of the present invention have been developed to provide for the use of multiple RNA expression cassettes, e.g., hairpin dsRNA, including shRNA as well as bi-finger and/or multi-finger dsRNA expression cassettes, from multiple promoters. The engineering of these multiple RNA pol III promoter vectors has been performed by selection of different promoter elements, together with spacing and orientation of expression cassettes within the recombinant expression vector to minimize the possibility of intra- or intermolecular recombination events. Assays to monitor the stability of such recombinant plasmids have been described previously (e.g. Focus 16:78, 1994, Gibco BRL Technical Bulletin (now Invitrogen Corp.)). Surprisingly, plasmid stability during bacterial fermentation and eukaryotic expression has been achieved despite the presence of multiple copies of palindromic or hairpin sequences, e.g., found in multiple (e.g., 2, 3, 4, 5) hairpin dsRNAs, as well as multiple copies of a polymerase III promoter sequence, e.g., 7SK and variants thereof, in the same or reverse orientation.

The multiple-promoter aspect of this invention in which each promoter controls expression of an independent RNA expression cassette, e.g., a shRNA expression cassette, is a critical feature in the design of, e.g., antiviral therapeutics, due to the nature of viral variation both within human populations and temporally within a host due to mutation events. For example, this aspect of the invention provides a means for delivering a multi-drug regimen comprising several different dsRNA viral inhibitor molecules to a cell or tissue of a host vertebrate organism, such that the level of viral inhibition is potentiated and the probability of multiple independent mutational events arising in the virus and rendering dsRNA inhibition of viral replication ineffective, would be infinitesimally small.

SUMMARY OF THE INVENTION

In general, this invention relates to novel nucleic acid expression constructs and methods of utilizing them to make biologically active nucleic acids, in particular short RNA effector molecules.

In one aspect, the invention relates to methods and compositions for expression of short hairpin RNAs (shRNA) including microRNAs (miRNA), wherein multiple and various forms of these molecules are generated simultaneously from 2, 3, 4, 5 or more polymerase III promoter elements within the same vector. By shRNA (short-hairpin RNA) is meant an RNA molecule of less than approximately 400 to 500 nucleotides (nt), preferably less than 100 to 200 nt, in which at least one stretch of at least 15 to 100 nucleotides (preferably 17 to 50 nt, more preferably 19 to 29 nt) is based paired with a complementary sequence located on the same RNA molecule, and where said sequence and complementary sequence are separated by an unpaired region of at least about 4 to 7 nucleotides (preferably about 9 to about 15 nucleotides) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, preferably about 9 to about 15 nucleotides, which forms a single-stranded loop above the stem structure created by the two regions of base complementarity. Included shRNAs are dual or bi-finger and multi-finger hairpin dsRNAs, in which the RNA molecule comprises two or more of such stem-loop structures separated by a single-stranded spacer region. In one aspect, the invention provides vector compositions comprising a plurality of RNA Polymerase III promoters, preferably human or mammalian RNA polymerase III promoters, which control the expression of multiple shRNA molecules with homology to RNA sequences from viruses causing human disease. The plurality of RNA polymerase III promoters may be the same or different. The invention provides the means of delivering to a host cell therapeutic and sustained amounts of 2, 3, 4, 5, or more different antiviral dsRNA hairpin molecules, in a genetically stable mode, which inhibits viral replication using 2, 3, 4, 5, or more independent viral sequence elements without evoking a dsRNA stress response. In one aspect, each RNA polymerase III promoter sequence is operably linked to a sequence encoding a different dsRNA hairpin molecule. In one aspect, one or more of said polymerase III promoters expresses an RNA transcript which forms a bi-fingered or dual dsRNA hairpin molecule comprising two or more shRNAs (each comprising a stem-loop structure) separated by a single-stranded region.

In one aspect, the invention relates to expression constructs comprising at least two different RNA polymerase III promoters, wherein each promoter is operably linked to a nucleic acid sequence encoding an RNA effector molecule. The RNA effector molecule may be any RNA of interest, including without limitation an shRNA, an antisense RNA, a ribozyme RNA, a triplex-forming RNA, an artificially selected high affinity RNA ligand (aptamer), a short hairpin double-stranded RNA, a microRNA, etc. The multiple RNA effector molecules may be the same or different; but by "at least two different RNA polymerase III promoters" Applicants mean that at least two of the promoters are "different" promoters; by different promoters, Applicants do not mean two copies of the same promoter located in different parts of the construct.

In one aspect, the invention further relates to a novel polymerase III promoter sequence as set forth in FIG. 4(e) herein.

BRIEF DESCRIPTION OF THE SEQUENCES

SEQ ID NO:1 represents nucleotides 1-240 of the human 7SK promoter with a Sal I restriction site inserted in place of nucleotides 235-240.
SEQ ID NO:2 represents nucleotides 250-381 of the human H1 promoter with a Sal I restriction inserted in place of nucleotides 376-381.
SEQ ID NO:3 represents nucleotides 65-335 of the human U6 promoter with a Sal I restriction site inserted in place of nucleotides 330-335.
SEQ ID NO:4 represents nucleotides 1-250 of the human 7SK promoter with a Sal I restriction site inserted in place of nucleotides 245-250.
SEQ ID NO:5 represents nucleotides 1-244 of a novel, human 7SK promoter with a Sal I restriction site inserted in place of nucleotides 235-240 and four adenine residues added 3' of the Sal I restriction site.
SEQ ID NO:6 represents HepB-based shRNA 2791.
SEQ ID NO:7 represents HepB-based shRNA 1907.
SEQ ID NO:8 represents HepB-based shRNA 1737.
SEQ ID NO:9 represents HepB-based shRNA 799.
SEQ ID NO:10 represents HepB-based shRNA 1991.
SEQ ID NO:11 represents HepB-based shRNA 1943.

BRIEF DESCRIPTION OF THE FIGURES

FIG. 1. Schematic drawing of tricistronic plasmid vectors containing 3 RNA polymerase III promoters, including 2 different eukaryotic RNA polymerase III promoters, controlling the expression of 3 different HBV-derived short hairpin RNA molecules. The 7SK promoter drives expression of shRNA 1737, one copy of the U6 promoter drives shRNA 2791, and a second copy of the U6 promoter drives expression of shRNA 1907. In Vector No. 40, the 7SK_1737 transcription unit is placed in the same functional orientation as the U6_2791 and the U6_1907 transcription units. In Vector No. 50, the orientation of the 7SK_1737 transcription unit is "flipped" such that its direction of transcription is oriented towards the U6_2791 transcription unit.

Figures 1, 7A:
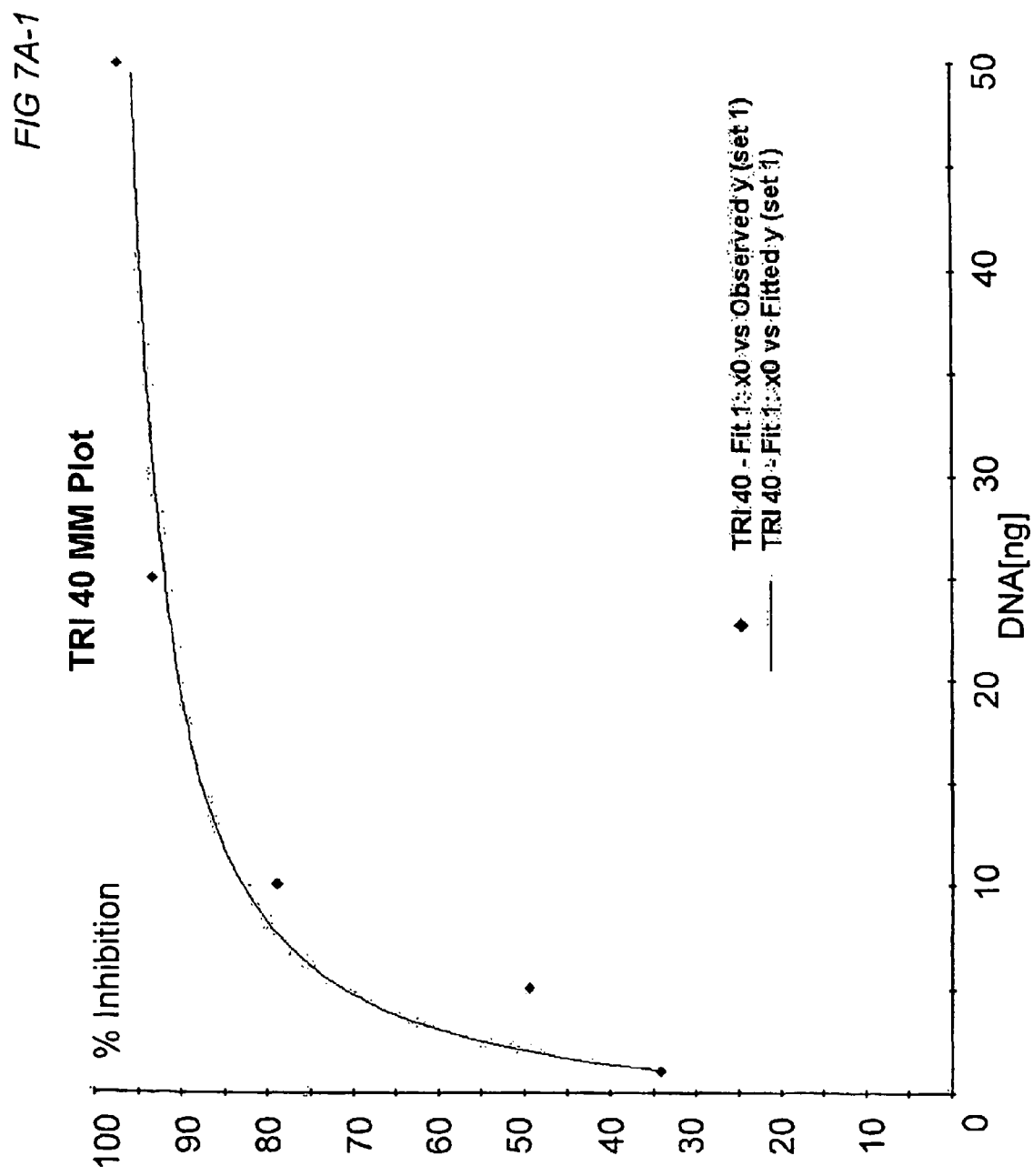
Figures 2, 7B:
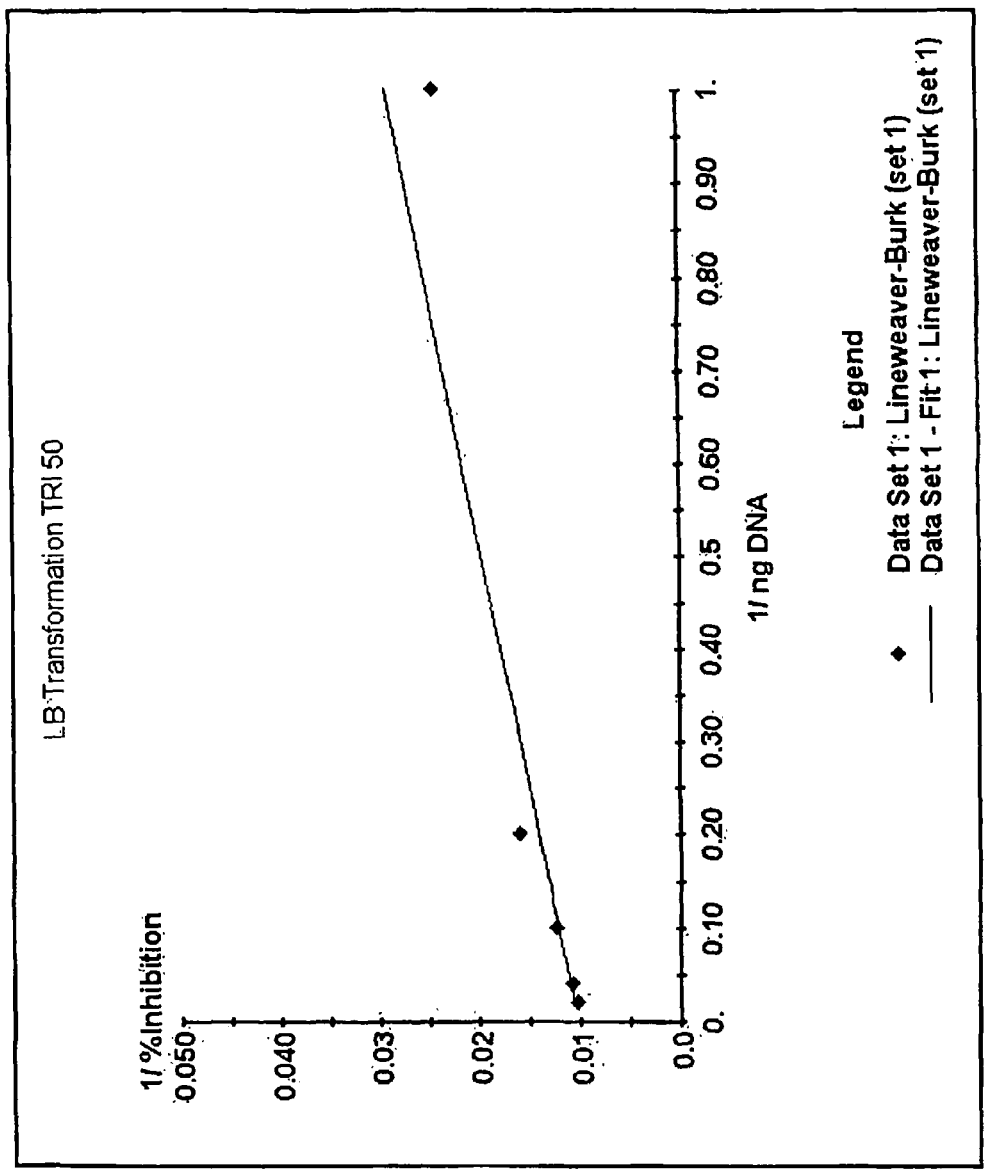

FIG. 2. Schematic drawing of tricistronic plasmid vectors, containing 3 different eukaryotic RNA polymerase III promoters controlling the expression of 3 different HBV-derived short hairpin RNA molecules. The 7SK promoter drives expression of shRNA 1737, the U6 promoter drives shRNA 2791, and the H1 promoter drives expression of shRNA 1907. In Vector No. 41, the 7SK_1737 transcription unit is placed in the same functional orientation as the U6_2791 and the H1_1907 transcription units. In Vector No. 51, the orientation of the 7SK_1737 transcription unit is "flipped" such that its direction of transcription is oriented towards the U6_2791 transcription unit.

FIG. 3. Results showing specific reduction of hepatitis B target RNA levels by transfection of tricistronic constructs expressing three different short dsRNA hairpin molecules. The assay employs synthetic RNA targets which fuse the HepB sequences to a functional luciferase mRNA (see text for details on the fusion assay and synthetic constructs).

FIG. 4 a, b, c, d, e. The sequences of the human 7SK (GenBank® Accession No. X04992, bases 1-234 [a,e], bases 1-244 [d] (SEQ ID NO: 1)), human H1 (GenBank®Accession No. X16612, bases 250-375 (SEQ ID NO: 2)) and human U6 (GenBank® Accession No. M14486, bases 65-329 (SEQ ID NO: 3)) promoters, respectively used in tricistronic constructs of the invention. A restriction site (the example of Sal I is given) used for insertion of shnRNA sequences is shown in upper case type. Other restriction site sequences can be substituted as desired. The 7SK promoters in a and d (SEQ ID NO: 4) represent the sequences of the natural promoters from bases 1-234 and bases 1-244, respectively, while the promoter in e (SEQ ID NO: 5) is a novel, synthetic improvement where 4 A residues are added 3' of the restriction site for enhanced function.

FIG. 5. The DNA sequences (5' to 3') encoding HBV based shRNAs (SEQ ID NOs: 6-11) expressed by vectors disclosed in this application. The sequences shown consist of 21 bases (19 bases in shRNA 1907) corresponding to the highly conserved HBV target sequence, followed by 9 bases encoding the loop portion of the hairpin, in turn followed by 21 bases which are the reverse complement of the first 21 bases and therefore form the double-stranded stem region by base pairing with the first 21 bases. Not shown are additional 5' and 3' sequences present in the dsRNA hairpin molecule: 5' leader nucleotides transcribed from restriction site sequence or promoter sequences downstream of the transcription initiation site, as well as multiple 3' terminal T (U) residues not homologous to the target which are incorporated into the RNA transcript during transcription termination.

FIG. 6. Table of calculated percent inhibition (IC50 values), relative to replicon-only control, of HBV surface antigen expression by tricistronic constructs in cell culture model of HBV replication.

FIG. 7. Graphs indicating dose response relationship between varying amounts of triscistronic vector constructs and inhibition of HBV surface antigen expression. 7a) determination of dose-response and IC50 values for HBV sAg inhibition by test vector 40. 7b) determination of dose-response and IC50 values for HBV sAg inhibition by test vector 50.

Figure 8:
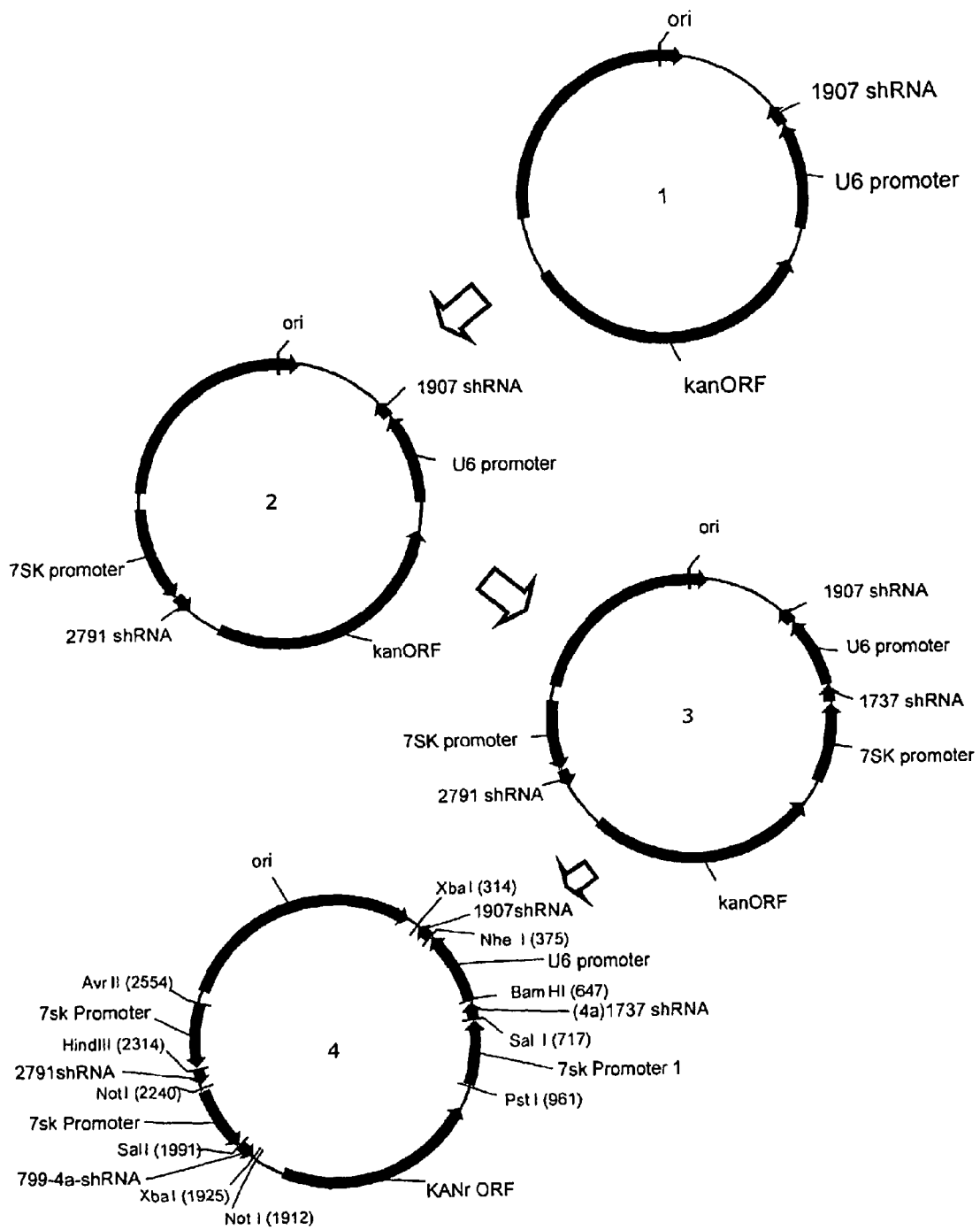

FIG. 8. Stepwise series of shRNA expression vectors numbered from 1 to 4 indicating the number of polymerase III promoter/shRNA cassettes. Each vector contains the prokaryotic pUC-derived origin of replication and a chimeric kanamycin resistance gene as described in the text. The 2 modified 7SK promoters (7SK-4A) present in vector 4 are indicated by the 4a or 4A nomenclature as part of the shRNA designation.

Figure 9:
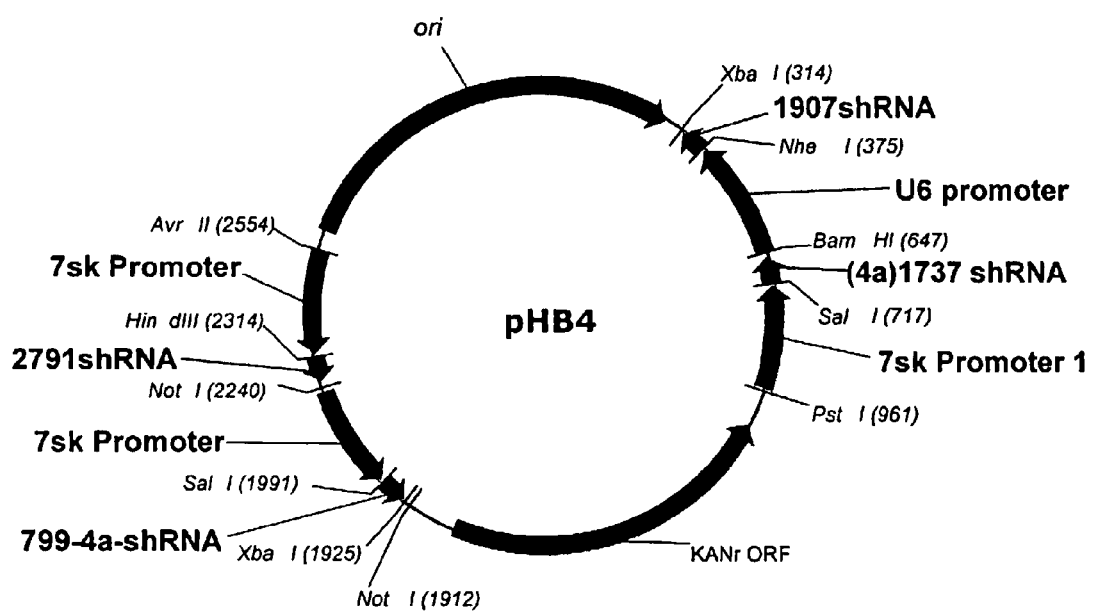

FIG. 9. Diagram of the pHB4 vector, which utilizes four polymerase III promoters to express four short dsRNA hairpin molecules, i.e., U6, 7SK, and two copies of the variant 7SK4A promoter. A five-cistron vector, pHB5, was also constructed, utilizing five polymerase III promoters—including four 7SK promoters (three variant 7SK4A promoters and one 7SK promoter as described in FIG. 4a) and one U6 promoter—to express five different short dsRNA hairpin molecules, each comprising a double-stranded stem region homologous and complementary to a highly conserved HBV sequence.

FIG. 10. Table showing results of testing the pHB4 vector and single-shRNA expression vectors against HBV sequence targets present in luciferase reporter constructs. For the pHB4 vector, 3 independent experiments are shown, each value comprises an average of 3 transfection replicates, each value therein comprising 3 luciferase determination replicate assays. The values given are the ratio of light units detected in the presence of shRNA vector to the light unit values produced by transfection of the reporter construct alone, multiplied by 100. Transfections were performed with Lipofectamine™ (Invitrogen Corp.) and luciferase assay reagents were obtained from Promega Inc.

FIG. 11. Table showing the effects of combining 3 different promoter elements, U6, 7SK, or 7SK4a, with 3 different HBV dsRNA hairpin sequences (1737, 1943, and 799) on expression of HBV surface antigen (sAg) and e antigen (eAg) in cells expressing HBV replicons. See text for sAg assay description. The eAg ELISA assays were essentially similar to the sAg assays except that the eAg antibody is substituted for sAg antibody. The IC50 values are given in ng per ml.

FIG. 12. Table showing a progressive decrease in IC50 values for sAg and eAg inhibition with increasing number (from 1 to 4) of promoter/HBV shRNA expression cassettes in a plasmid vector, corresponding to vectors diagrammed in FIG. 8.

FIG. 13. Expression of two different shRNA domains within a single RNA molecule (bi-finger and dual hairpin construct) transcribed from a single Pol III promoter. The top of the figure shows diagrams of the short spacer and long spacer forms of the RNA. The table shows the level of inhibition of the luciferase reporter containing the complete HBV genome and the reporters containing only the 1737 or 2791 target sequences. The short spacer contains 16 nt between the hairpins and the long spacer contains 42 nt between the hairpins. The data are expressed as the ratio of light units of each reporter construct to the luciferase-only (no HBV sequences) reporter construct, multiplied by 100. In one aspect, the expression constructs of the invention can express two, three or more dsRNA hairpins from one or more of the polymerase III promoter transcription units contained therein, as shown in this FIG. 13.

Figure 14:
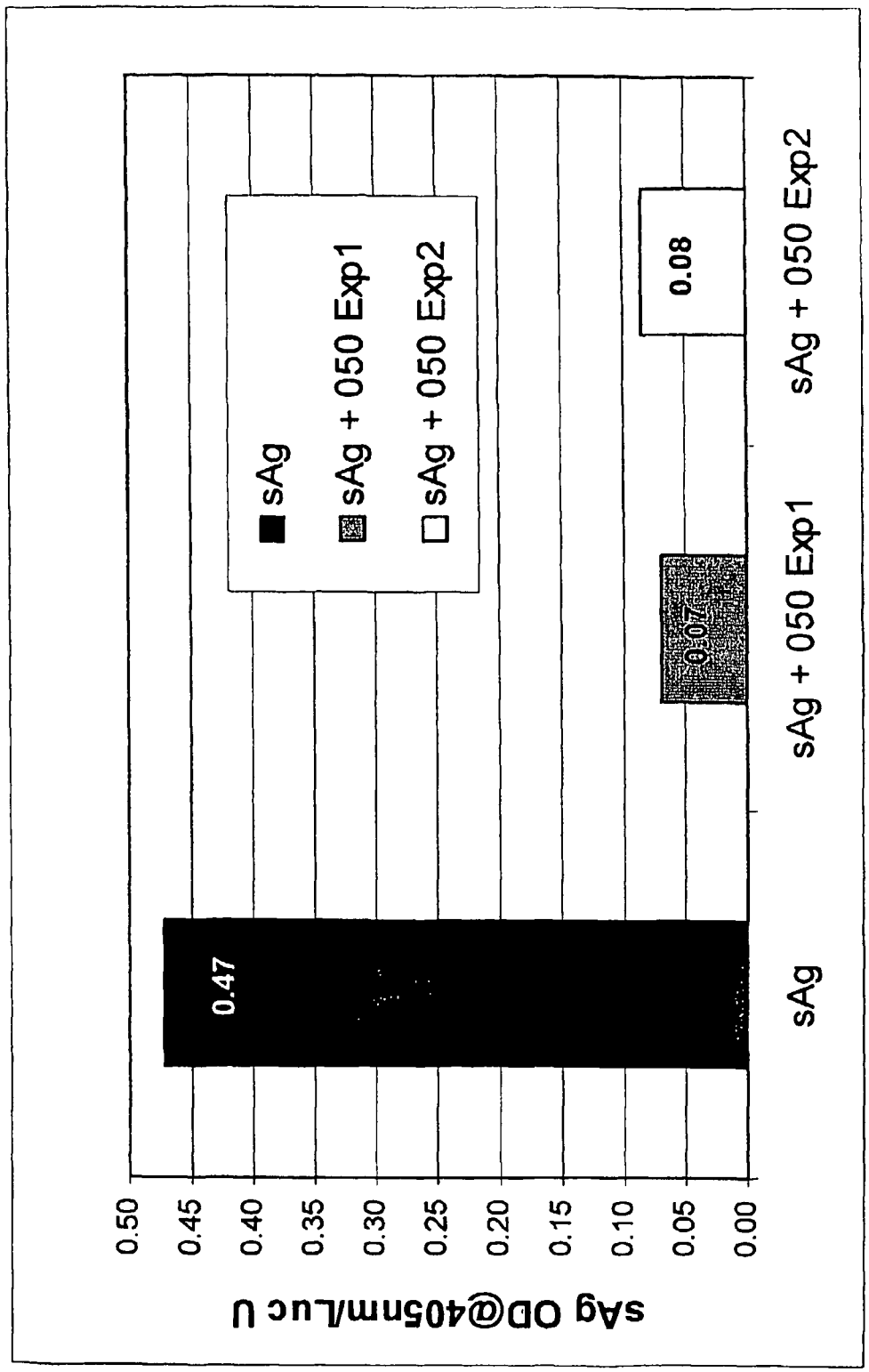

FIG. 14. In vivo expression of HBV sAg from a liver-specific promoter vector in the absence (solid bar) or presence of co-injected pHB4 vector, which expresses four different HBV dsRNA hairpin molecules. The data are the average of three mice per group, with two replicate groups (Exp 1 and Exp 2). Values are given as the ratio sAg ELISA optical density values to luciferase light units, i.e., normalized to the coinjected luciferase expression plasmid (see text). Luciferase values were determined from liver cells whereas the sAg assays were performed on mouse serum.

Figure 15:
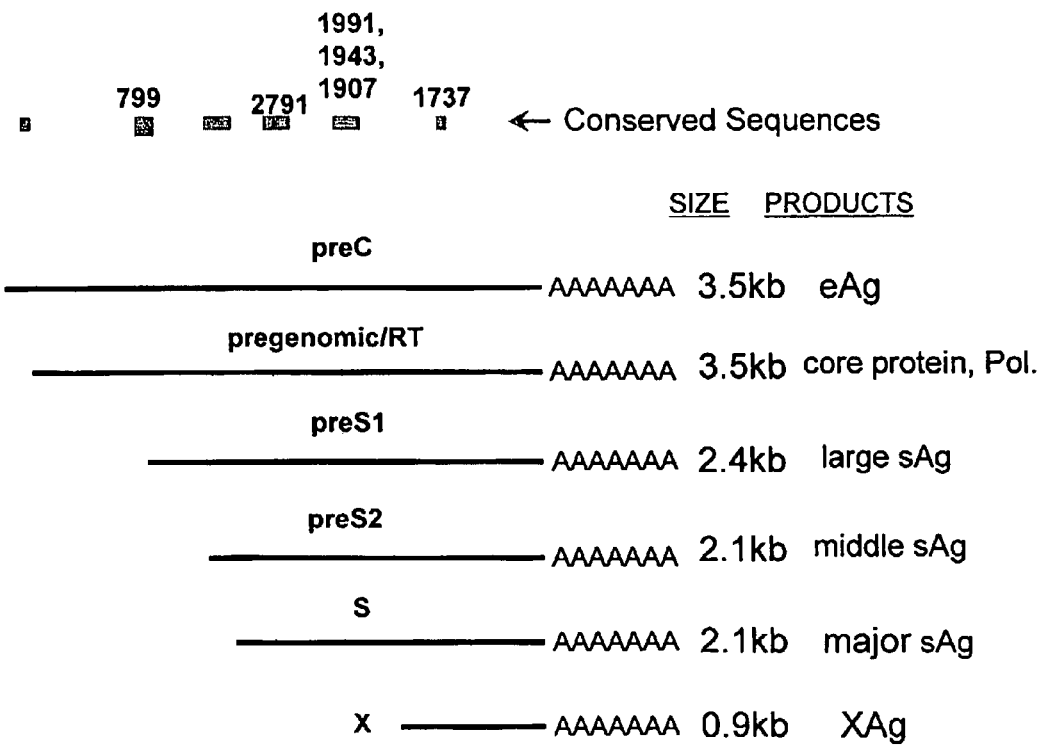

FIG. 15. Schematic diagram showing the positions of conserved regions of sequence among hundreds of available HBV isolates (see text), and indicating the location of sequences and regions corresponding to the selected HBV dsRNA hairpin targets described in this application. The diagram depicts the nature of the collinear transcripts of HBV and indicates the protein product that is made from each transcript. Thus, for example, it can be seen that only the 1737 dsRNA hairpin is capable of targeting the HBV X-protein while, e.g., the 799 dsRNA hairpin can inhibit HBV eAg expression but is not capable of directly interfering with HBV sAg expression. Thus, by simultaneously delivering a diverse selection of dsRNA molecules against HBV, the expression constructs of the invention provide a multi-drug regimen against HBV which not only contributes to a high level of viral inhibition, but militates against the development of viral resistance.

DETAILED DESCRIPTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Definitions: In the present disclosure, the following terms below are used according to the customary understanding of those skilled in this art, as more particularly defined herein.

By "expression construct" is meant any double-stranded DNA or double-stranded RNA designed to transcribe an RNA of interest, e.g., a construct that contains at least one promoter which is or may be operably linked to a downstream gene, coding region, or polynucleotide sequence of interest (e.g., a cDNA or genomic DNA fragment that encodes a polypeptide or protein, or an RNA effector molecule, e.g., an antisense RNA, triplex-forming RNA, ribozyme, an artificially selected high affinity RNA ligand (aptamer), a double-stranded RNA, e.g., an RNA molecule comprising a stem-loop or hairpin dsRNA, or a bi-finger or multi-finger dsRNA or a microRNA, or any RNA of interest). An "expression construct" includes a double-stranded DNA or RNA comprising one or more promoters, wherein one or more of the promoters is not in fact operably linked to a polynucleotide sequence to be transcribed, but instead is designed for efficient insertion of an operably-linked polynucleotide sequence to be transcribed by the promoter. Transfection or transformation of the expression construct into a recipient cell allows the cell to express an RNA effector molecule, polypeptide, or protein encoded by the expression construct. An expression construct may be a genetically engineered plasmid, virus, recombinant virus, or an artificial chromosome derived from, for example, a bacteriophage, adenovirus, adeno-associated virus, retrovirus, lentivirus, poxvirus, or herpesvirus, or further embodiments described under "expression vector" below. An expression construct can be replicated in a living cell, or it can be made synthetically. For purposes of this application, the terms "expression construct", "expression vector", "vector", and "plasmid" are used interchangeably to demonstrate the application of the invention in a general, illustrative sense, and are not intended to limit the invention to a particular type of expression construct.

By "expression vector" is meant a DNA construct that contains at least one promoter which is or may be operably linked to a downstream gene, coding region, or polynucleotide sequence to be transcribed (e.g., a cDNA or genomic DNA fragment that encodes a protein, optionally, operably linked to sequence lying outside a coding region, an antisense RNA coding region, or RNA sequences lying outside a coding region). An "expression construct" may also be a DNA construct comprising one or more promoters, wherein one or more of the promoters is not in fact operably linked to a polynucleotide sequence to be transcribed, but instead is designed for efficient insertion of an operably-linked polynucleotide sequence to be transcribed by the promoter. Transfection or transformation of the expression vector into a recipient cell allows the cell to express RNA encoded by the expression vector. An expression vector may be a genetically engineered plasmid, virus, or artificial chromosome derived from, for example, a bacteriophage, adenovirus, adeno-associated virus, retrovirus, poxvirus, or herpesvirus. Such expression vectors can include sequences from bacteria, viruses or phages. Such vectors include chromosomal, episomal and virus-derived vectors, e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. Thus, one exemplary vector is a double-stranded DNA phage vector. Another exemplary vector is a double-stranded DNA viral vector. In one aspect, the invention relates to expression vectors, plasmids, and constructs as described herein, which are isolated and purified so as to be useful for any of a variety of applications, e.g., as a reagent for scientific research, for human and/or veterinary use for therapeutic and/or prophylactic pharmaceutical purposes.

In some aspects two or more expression constructs will be used as a single composition, as e.g., a pharmaceutical composition, or a research reagent. In some aspects, the two or more expression constructs will be used in two or more compositions used in concert, as for example, administered simultaneously or within a period of minutes, hours or days of each other, e.g., within one, two, three days, or even a week of each other; so long as there will be some functional or physiological interaction between the products of each construct delivered to the eukaryotic cell. The expression construct(s) collectively comprise at least two, three, four or more RNA polymerase III promoters, in some aspects at least two different RNA polymerase III promoters, wherein each promoter is or may be operably linked to a nucleotide sequence encoding an RNA effector molecule. In one aspect, the expression system serves to provide a single cell with one or more expression constructs comprising at least two different RNA polymerase III promoters, wherein each promoter is operably linked to a nucleotide sequence encoding an RNA effector molecule. In one aspect, the expression system will be a single expression construct or two or more expression constructs, e.g., a plasmid or plasmids, comprising two or more promoters, e.g., two, three, four, five, six, seven, eight, or more, comprising in some aspects at least two different RNA polymerase III promoters, wherein each promoter is or may be operably linked to a nucleotide sequence encoding an RNA effector molecule.

By "nucleic acid molecule" or "polynucleotide" is meant a polymeric compound made up of a linear sequence of subunits known as nucleotides; each nucleotide has three components: one or more phosphate groups linked to a sugar (e.g., a pentose or hexose), which in turn is linked to a nitrogen-containing base derived from purine (e.g., adenine or guanine) or from pyrimidine (e.g., thymine, cytosine, or uracil). The nucleotides are joined together into polynucleotides through phosphate linkages between adjacent sugar units. Polynucleotide molecules may be single-stranded, such as most naturally occurring RNA (ribonucleic acid) molecules, or double-stranded, such as most naturally occurring DNA (deoxyribonucleic acid) molecules. In double-stranded nucleic acid molecules, the bases of one strand are paired with the bases on the other strand in a complementary manner. The purine base adenine (A) always pairs with the pyrimidine base thymine (T) in DNA [or uracil (U) in RNA]; the purine base cytosine (C) always pairs with the pyrimidine base guanine (G). Each basepair includes one purine and one purimidine. Because an adenine on one strand is always paired with a thymine (or uracil) on the other strand and a cytosine is always paired with a guanine, the two strands are said to be complementary to each other and the sequence of one strand can be deduced from the sequence of its complement strand. Particular naturally-occurring nucleic acid molecules include genomic deoxyribonucleic acid (DNA) and genomic ribonucleic acid (RNA), as well as the several different forms of the latter, e.g., messenger RNA (mRNA), transfer RNA (tRNA), and ribosomal RNA (rRNA), as well as catalytic RNA structures such as ribozymes and regulatory RNAs such as microRNAs (miRNAs). Also included are different DNA molecules which are complementary (cDNA) to the different RNA molecules. Synthesized DNA, or a hybrid thereof with naturally-occurring DNA, as well as DNA/RNA hybrids, and PNA molecules (Gambari, *Curr. Pharm. Des.* 7:1839-62 (2001)) are also included within the definition of "nucleic acid molecule."

It is contemplated that where the desired nucleic acid molecule is RNA, the T (thymine) in the sequences provided herein is substituted with U (uracil). For example, shRNA 2791, shRNA 1907, and shRNA 1737 are disclosed herein as DNA sequences. It will be obvious to one of ordinary skill in the art that an RNA effector molecule comprising sequences from any of the aforementioned sequences will have U substituted for T.

Nucleic acids typically have a sequence of two or more covalently bonded naturally-occurring or modified deoxyribonucleotides or ribonucleotides. Modified nucleic acids include, e.g., peptide nucleic acids and nucleotides with unnatural bases.

The term "operably linked" refers to functional linkage between a nucleic acid expression control sequence (such as a promoter, signal sequence, enhancer or array of transcription factor binding sites) and a second nucleic acid sequence, wherein the expression control sequence affects transcription and/or translation of the nucleic acid corresponding to the second sequence when the appropriate molecules (e.g., transcriptional activator proteins) are bound to the expression control sequence. The expression constructs of the invention comprising two or more RNA polymerase III promoters may comprise a nucleic acid sequence encoding an shRNA, dsRNA hairpin or microRNA operably linked to one, two, or to each of said promoters, or in one aspect the invention relates to an expression construct comprising two, three, four, five, or multiple RNA polymerase III promoter expression cassettes, designed for convenient insertion into each expression cassette of a selected sequence to be transcribed, e.g., using appropriately selected cloning site(s), e.g., comprising selected restriction sites.

In the expression constructs or vectors of the invention, the RNA polymerase III promoters are "isolated" in the sense that they are not operably linked to a gene or RNA sequence with which they are operably linked in their normal cellular environment, e.g., in the expression constructs of the invention the 7SK promoter is not operably linked to the 7SK gene, the U6 promoter is not operably linked to the U6 gene, and the H1 promoter is not operably linked to the H1 gene, etc.

By a "promoter" is meant a nucleic acid sequence sufficient to direct transcription of an operably linked nucleic acid molecule. Also included in this definition are those transcription control elements (e.g., enhancers) that are sufficient to render promoter-dependent gene expression controllable in a cell type-specific, tissue-specific, or temporal-specific manner, or that are inducible by external signals or agents; such elements, which are well-known to skilled artisans, may be found in a 5' or 3' region of a gene or within an intron. See, e.g., Published U.S. Patent Application No. 2005/0130184 A1, 16 Jun. 2005, Xu et al., directed to modified polymerase III promoters which utilize polymerase II enhancer elements, as well as Published U.S. Patent Application No. 2005/0130919 A1, 16June 2005, Xu et al., directed to regulatable polymerase III and polymerase II promoters, the teaching of which is hereby incorporated by reference. Desirably, a promoter is operably linked to a nucleic acid sequence, for example, a cDNA or a gene sequence, or an effector RNA coding sequence, in such a way as to enable expression of the nucleic acid sequence, or a promoter is provided in an expression cassette into which a selected nucleic acid sequence to be transcribed can be conveniently inserted.

By "RNA polymerase III promoter" or "RNA pol III promoter" or "polymerase III promoter" or "pol III promoter" is meant any invertebrate, vertebrate, or mammalian promoter, e.g., human, murine, porcine, bovine, primate, simian, etc. that, in its native context in a cell, associates or interacts with RNA polymerase III to transcribe its operably linked gene, or any variant thereof, natural or engineered, that will interact in a selected host cell with an RNA polymerase III to transcribe an operably linked nucleic acid sequence. By U6 promoter (e.g., human U6, murine U6), H1 promoter, or 7SK promoter is meant any invertebrate, vertebrate, or mammalian promoter or polymorphic variant or mutant found in nature to interact with RNA polymerase III to transcribe its cognate RNA product, i.e., U6 RNA, H1 RNA, or 7SK RNA, respectively. Preferred in some applications are the Type III RNA pol III promoters including U6, H1, and 7SK which exist in the 5' flanking region, include TATA boxes, and lack internal promoter sequences. Internal promoters occur for the pol III 5S rRNA, tRNA or VA RNA genes. The 7SK RNA pol III gene contains a weak internal promoter and a sequence in the 5' flanking region of the gene necessary for transcription. RNA pol III promoters include any higher eukaryotic, including any vertebrate or mammalian, promoter containing any sequence variation or alteration, either natural or produced in the laboratory, which maintains or enhances but does not abolish the binding of RNA polymerase III to said promoter, and which is capable of transcribing a gene or nucleotide sequence, either natural or engineered, which is operably linked to said promoter sequence. Pol III promoters for utilization in an expression construct for a particular application, e.g., to express RNA effector molecules such as hairpin dsRNAs against a fish, bird, or invertebrate virus may advantageously be selected for optimal binding and transcription by the host cell RNA polymerase III, e.g., including avian pol III promoters in an expression construct designed to transcribe a plurality of hairpin dsRNAs against an avian virus such as West Nile Virus or avian influenza virus ($H_5N1$) in avian host cells and utilizing instead human or other mammalian pol III promoters in an expression construct designed to transcribe a plurality of hairpin dsRNAs against an avian virus such as West Nile Virus or avian influenza virus ($H_5N1$) in human host cells.

By "multiple polymerase III promoter vector" or "multiple pol III promoter expression construct" or similar expressions, is meant any vector, plasmid, or expression construct which contains at least two polymerase III promoters. In one aspect, the multiple polymerase III promoter vector will contain at least two different polymerase III promoters. By "different" polymerase III promoters is meant any two RNA polymerase III promoters, including variants such as polymorphisms and mutants thereof, which in a particular species will drive transcription of different cognate transcripts, such as, e.g., the human 7SK promoter, the human U6 promoter, and the human H1 promoter, which are considered three "different" polymerase III promoters. Also intended by Applicants as "different" polymerase III promoters will be corresponding polymerase III promoters from different species, such as, e.g., a human U6 vs. a murine U6 promoter will be different promoters; a human H1 vs. a murine H1 promoter will be different; or a human 7SK promoter and a murine 7SK promoter will be considered different promoters. Therefore, the various 7SK promoters described in FIG. 4(a), 4(d), and 4(e) are considered variants of the "same" promoter, the 7SK promoter. In some aspects, multiple copies of the "same" polymerase III promoter may be included in an expression construct of the invention so long as two "different" RNA polymerase III promoters are also included; e.g., three 7SK promoters (e.g., 7SK 256 promoter, two 7SK 4A promoters) and one H1 promoter; or four 7SK promoters (7SK 256 promoter, three 7SK 4A promoters) and one U6 promoter. In some aspects, the expression constructs of the invention may contain multiple copies of the same polymerase III promoter without a "different" polymerase III promoter; e.g., three, four, five, six or more 7SK promoters each operably linked to a sequence encoding a shRNA. Optionally, in some embodiments, other promoters may be included in addition to the two or more polymerase III promoters, e.g., one or more polymerase I promoters and/or one or more polymerase II promoters, one or more mitochondrial promoters, etc. In one aspect, an expression construct comprising multiple polymerase III promoters (2, 3, 4, 5, or more) is engineered to express multiple dsRNA hairpins or shRNAs, in which case 2, 3, 4, 5, or more copies of the same pol III promoter may be used, irrespective of whether or not a "different" RNA polymerase III promoter is also included.

In the general practice and use of recombinant DNA and synthetic vectors for RNA expression in eukaryotic cells, the majority of engineering efforts have been directed towards expression of protein-coding RNA molecules. With the advent of antisense RNA and, more recently, the phenomenon of gene silencing by RNA interference (via double-stranded RNA, abbreviated "dsRNA") it has been necessary to develop expression systems suitable for generating short, non-protein encoding RNA molecules that are essentially catalytic in nature. This has required the adaptation of several classes of natural promoters that have evolved to generate natural, small RNA molecules (such as ribosomal RNAs, spliceosome RNAs, RNAse P structural RNA components et al.), and these promoters are generally classed as RNA Polymerase I and RNA Polymerase III ("Pol III") promoters. The RNA polymerase III promoters are admirably adapted to expression of such short RNA transcripts, up to a maximum of about 400 to 500 nucleotides in length. Within the RNA Pol III family, there is further subdivision of natural promoters into 3 subtypes (1, 2 and 3) which are structurally distinct, but also reflect specialization as to which subcellular compartment their products will be utilized in. For example, the U6 genes encode small nuclear RNAs which function in the nucleus during RNA splicing, whereas various tRNA genes encode tRNA molecules which function in the cytoplasm during protein synthesis. Thus, one aspect of the present invention is the use and construction of vectors containing multiple Pol III promoters comprising one or more representatives of the type 3 promoters (e.g U6, H1, 7SK, as well as sequence variants thereof, such as the 7SK 4A sequence variant shown herein to provide superior expression of short RNA effector molecules, e.g., short dsRNA hairpin molecules) and members of the type1 or type 2 subclasses (e.g. various tRNA gene promoters). Such combinations of promoters provide a means for regulating the relative distribution (nucleus vs. cytoplasm) of shRNA and/or microRNA products within the cell. Experimental examples of this localization has been described in several publications, for example lives et al., *Gene* 171:203-08 (1996); Kawasaki and Taira, *Nucleic Acids Res.* 31:700-07 (2003); and Boden et al., *Nucleic Acids Res.* 31:5033-38 (2003).

A further aspect of the present invention relates to the requirement for multiple Pol III promoters where the vector is designed to express multiple (at least 2 but preferably 3, 4, 5 or more) "RNA effector molecules". RNA effector molecules suitable for expression by RNA polymerase III promoters are short RNA transcripts of up to about 400 to 500 nucleotides in length, including, but are not limited to, antisense RNA, ribozyme RNA, hairpin dsRNA, microRNA and duplex dsRNA molecules. Preferred RNA effector molecules are short hairpin dsRNA (shRNA) molecules, triplex-forming RNA, ribozymes, an artificially selected high affinity RNA ligand (aptamer), a double-stranded RNA, e.g., an RNA molecule comprising a stem-loop or hairpin dsRNA, or a bi-finger or multi-finger dsRNA or a microRNA, or any short RNA of interest.

By "shRNA" or "short-hairpin RNA" or "dsRNA hairpin" is meant an RNA molecule of less than approximately 400 to 500 nucleotides (nt) in length, preferably less than 100 to 200 nt in length, in which at least one stretch of at least about 15 to 100 nucleotides (preferably 17 to 50 nt; more preferably 19 to 29 nt) is base paired with a complementary sequence located on the same RNA molecule, and where said sequence and complementary sequence are separated by an unpaired region of at least about 4 to 7 nucleotides (preferably about 9 to about 15 nucleotides) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides; preferably about 9 to about 15 nucleotides, which forms a single-stranded loop above the stem structure created by the two regions of base complementarity. Included shRNAs are dual or bi-finger and multi-finger hairpin dsRNAs, in which the RNA molecule comprises two or more of such stem-loop structures separated by single-stranded spacer regions. Applicants intend that an expression construct of the invention may express multiple copies of the same, and/or one or more, including multiple different, short hairpin RNA molecules. Short hairpin RNA molecules considered to be the "same" as each other are those that comprise only the same double-stranded sequence, and short hairpin RNA molecules considered to be "different" from each other will comprise different double-stranded sequences, regardless of whether the sequences to be targeted by each different double-stranded sequence are within the same, or a different gene, such as, e.g., sequences of a promoter region and of a transcribed region (mRNA) of the same gene, or sequences of two different genes.

In one embodiment of this invention, a recombinant vector is engineered to encode multiple, e.g., three, four, five or more short hairpin dsRNAs, each expressed from a different expression cassette comprising a polymerase III promoter, one or more, including all of which, may be different from the others. In one aspect of the invention, a recombinant expression vector transcribing three, four, five or more different shRNA molecules (each comprising a double-stranded "stem" region homologous and complementary to a conserved HBV sequence) is used to inhibit replication of hepatitis B virus (HBV) and each shRNA molecule is expressed under the control of a Pol III promoter, e.g., 7SK, H1, and U6, which may be the same of different. In one aspect, a recombinant expression vector of the invention may express one or more bi-fingered or multi-fingered dsRNA hairpin molecules from one or more polymerase III promoter-driven transcription units as well as one or more single hairpin dsRNA molecules from one or more polymerase III promoter-driven transcription units. It will be understood that in any of the expression constructs of the invention transcribing a hairpin dsRNA from a polymerase III promoter, the hairpin dsRNA may be a single hairpin dsRNA or a bi-fingered, or multi-fingered dsRNA hairpin as described in WO2004/035765, published 29 Apr. 2004, or a partial or forced hairpin structure as described in WO2004/011624, published 5 Feb. 2004, the teaching of which is incorporated herein by reference.

By "target sequence to be inhibited" or "target sequence" is meant a nucleotide sequence in a host cell which is inhibited, down-regulated, modulated, repressed, or silenced in a sequence-specific manner through any mechanism, including antisense inhibition, ribozyme cleavage, aptamer inhibition, and/or through the phenomenon of RNAi or double-stranded RNA (dsRNA)-mediated gene silencing, by expression in said host cell of an appropriate RNA effector molecule. The degree of inhibition, modulation, or silencing achieved will vary with the nature and quantity of the expression construct provided to the host cell, the identity, nature, and level of expression of the RNA effector molecule(s) produced, the time after administration, etc., but will be evident e.g., as a detectable decrease in target gene expression (level of mRNA or protein) and/or related target or cellular function, or e.g., decrease in level of viral replication, etc.; desirably a degree of inhibition greater than 10%, 33%, 50%, 75%, 90%, 95% or 99% as compared to a cell not treated according to the present invention will be achieved. The target sequence to be inhibited may be an endogenous sequence to be inhibited or silenced, such as, e.g., a nucleotide sequence associated with a disease or disorder such as, e.g., certain cancers, Huntington's disease or age-related macular degeneration, or a pathogen-associated nucleotide sequence, present in the host cell. In one aspect, the target sequence will be inhibited through RNAi or double-stranded RNA (dsRNA)-mediated gene silencing, in which a dsRNA complementary to a region of a target gene in a cell or organism inhibits expression of the target gene, including post-transcriptional gene silencing (PTGS) in which transcription of the target locus is not affected, but the RNA half-life is decreased and/or transcriptional gene silencing (TGS) in which transcription of a gene is inhibited. (See, e.g., WO99/32619, published 1 Jul. 1999, Fire et al.; U.S. Pat. No. 6,506,559: "Genetic Inhibition by Double-Stranded RNA"; and WO00/63364: "Methods and Compositions for Inhibiting the Function of Polynucleotide Sequences," Pachuk and Satishchandran; including the various RNAi targets identified therein.) For TGS induction, the selected dsRNA target sequences will desirably contain a promoter sequence, a subset of a promoter sequence, a promoter sequence/transcription initiation site sequence, or another regulatory region sequence, optionally in combination with a sequence operably linked to such promoter/regulatory region in the DNA or RNA target. For induction of PTGS, the selected dsRNA target sequences may contain only coding and/or 3' and/or 5' UTR sequences, or may desirably contain a combination of coding and/or UTR sequence and/or promoter sequences. In one aspect, the target sequences will be sequences of a pathogen, e.g., a viral pathogen, infecting a host cell, e.g., an invertebrate or vertebrate host cell, preferably a mammalian cell, including a human cell. In one aspect, the target sequence will be a nucleic acid sequence of a viral pathogen associated with a chronic disease in a selected host organism, such as hepatitis viruses, e.g., HBV, HCV, as well as viruses such as HIV, SIV, etc.

Since RNA interference acts in a sequence specific manner, the RNAi molecule used as a drug must be specific to its target. It is known in the art that viral genomes are variable to accommodate resistance to changes in the environment. Thus, in order to knock down viral genome replication using RNAi, there is a need to identify conserved and unique regions in the viral genome. It is equally important to ensure that conserved viral sequences targeted for silencing according to the invention be substantially non-homologous to any naturally occurring, normally functioning, host polynucleotide sequence, so that the dsRNA molecule does not adversely affect the function of any essential, naturally occurring, host polynucleotide sequences, when used in the methods of this invention. Such naturally occurring functional polynucleotide sequences include sequences that encode desired proteins, as well as sequences that are non-coding but essential regulatory sequences in a healthy host organism.

Methods and compositions relating to the selection of HBV and/or HCV sequences for shRNA design are hereby incorporated by reference to WO2005/014806, published 17 Feb. 2005, and U.S. Provisional Application Ser. No. 60/638, 294, filed 22 Dec. 2004 (Conserved HBV and HCV Sequences Useful for Gene Silencing), as well as U.S. Provisional Application Ser. No. 60/613,065, filed 24 Sep. 2004 (Targeting Opposite Strand Replication Intermediates of Single-Stranded Viruses by RNAi). A major therapeutic advantage of the multiple shRNA approach is that significant pathogens, especially viruses such as the HBV, HCV, and HIV viruses undergo mutation during their course of infection in a host or patient, and throughout the population. By including multiple sequence targets in the multiple short hairpin dsRNA-based therapeutic, the probability of mutations such that a virus "escapes" from detection and inactivation by the multiple shRNAs becomes practically zero.

With respect to the inclusion of multiple promoters within the same expression vector or expression system, engineering alternatives must be incorporated into the vector design to avoid two types of problems that can occur when using multiple promoters. One problem, exemplified by "transcriptional interference" relates to the enzymology and topology of transcribing multiple sites on a DNA plasmid template simultaneously. The second type of problem involves recombinational events which could be potentiated by having multiple copies of a homologous sequence element within the same plasmid. The selection and disposition of promoter elements in the compositions of this invention have been performed to minimize or eliminate each of these deleterious possibilities. Further detail on these phenomena is provided below.

Transcription from a DNA molecule affects the supercoiling of the template DNA ahead of the growing strand and behind the just transcribed strand (Dunaway and Ostrander, *Nature* 361:74648 (1993); Krebs and Dunaway, *Mol. Cell. Biol.* 16:5821-5829 (1996)). These changes in supercoiling affect the entire plasmid. Changes in supercoiling detrimentally affect the activity of many promoters and can in fact abolish activity. This means that activity from one promoter in an expression construct can negatively impact on the activity of another promoter and vice versa. Multiple promoters in a single expression construct, when both are active in the same compartment and running in the same direction, can result in promoter occlusion or promoter interference. Promoter interference occurs when promoters are situated near each other (within several hundred nucleotides). The nucleation of transcription factors and other factors on one promoter sterically hinders the nucleation of factors on the second promoter. Promoter occlusion is particularly a problem for systems in which a terminator is not located at the end of one cistron and before the next promoter. Since RNA pol II has no efficient termination system, this is a potential problem for the use of multiple RNA pol II promoters on the same expression construct. Promoter occlusion results when transcription from one cistron does not terminate at the end of the cistron and runs through a second promoter preventing transcription initiation from that promoter.

Transcription interference occurs when two active promoters both active in the same subcellular compartment are facing each other in the converging direction. Also transcription interference can occur in which a downstream promoter is repressed by the presence of an upstream promoter (both of which should be active at the same time on the same molecule). The extending transcript initiated from the upstream promoter represses initiation from the downstream promoter as the extending transcripts transverse the downstream promoter. (Proudfoot, *Nature* 322:562-65 (1986)). Transcription from one promoter can interfere with transcription from the other promoter and cause premature termination of the transcript.

Recombination can occur by sequence specific recognition of substantial stretches of homology among the sequences within a plasmid vector, such as would be the case if multiple copies of the same promoter or promoters with substantial homology were to be incorporated into the plasmid. Such recombination events could adversely affect the efficacy of any plasmid-based therapeutic (e.g., by rendering plasmid control elements dysfunctional) and could also have negative consequences for the safety of said vectors in human therapy. Recombination during bacterial fermentation of plasmid vectors represents a further problem. Recombination is recognized as a particular problem in plasmids encoding dsRNA hairpins because of the presence of inverted repeat or palindromic sequences which predispose to recombination events. Miyagishi and Taira, *Nat. Biotechnol.* 19:497-500 (2002). This potential problem could only be expected to increase in plasmid or other vectors encoding two, three, four, five or more hairpins, as well as two, three, four or more copies of the same promoter, or promoters having substantial homology to one another. Thus, in one aspect, the present invention provides for the use of multiple promoter elements which are non-identical in sequence. In another aspect, the invention provides expression constructs which include multiple promoter elements, wherein two, three or more may be identical in sequence or variant sequences of the same promoter element, e.g., two, three, or more 7SK, and/or modified 7SK promoter sequences, in addition to other different RNA Pol III promoters if desired, are utilized in a single expression construct, wherein each promoter sequence transcribes a selected dsRNA hairpin sequence, which may be the same or different. Surprisingly, plasmid expression vectors comprising 2, 3, 4, or more polymerase III promoters, which may be the same or different in sequence and orientation, transcribing 2, 3, 4, 5, or more dsRNA hairpin molecules may be made and used as taught herein.

The vectors of this invention may be constructed using standard recombinant DNA techniques known to those skilled in the art. There are three major types of components needed to generate these constructs: 1) a plasmid "backbone"; 2) promoter elements; and 3) nucleotide sequences encoding RNA(s) of interest, e.g., short hairpin RNA sequence elements. The vector backbone may be derived de novo from a variety of bacterial strains on deposit at resources such as the American Type Culture Collection (ATCC; Manassas, Va., USA) by isolating plasmid DNA from bacterial cultures. Alternatively, plasmid backbones specifically designed for multipurpose recombinant DNA engineering can be purchased commercially from a variety of suppliers, such as Stratagene (San Diego, Calif.), New England Biolabs (Beverly, Mass.), or Invitrogen (San Diego, Calif.). The plasmids contain the essential elements of 1) bacterial origin of replication, 2) bacterial antibiotic resistance marker, and 3) cloning sites for insertion of other DNA elements.

The RNA polymerase promoters used in this invention are known in the art and can be obtained by searching public sequence databases such as GenBank®. Examples of Pol III, Type 3 promoters to be found include those known as H1, 7SK, U6, and MRP. Variant forms, i.e., copies, of these promoters and the genes which they are a part of may exist in this database and may function equally or more effectively in this invention. For example, alternative, synthetic variant forms of the 7SK promoter useful in the composition and methods of the invention are disclosed in this application [see FIGS. 4 (*a*), (*d*), and (*e*)], which comprise truncated or extended lengths and/or nucleotide substitutions with respect to the canonical 7SK promoter, as presented in the GenBank® database. Human or other mammalian RNA Pol III polymerase, Type 3 promoters are preferred, e.g., human or murine 7SK, H1, and U6, for applications involving expression by an endogenous RNA III polymerase in a mammalian host cell. For applications involving expression by an endogenous RNA III polymerase in a non-mammalian host cell, e.g., in an avian, fish, or invertebrate host cell, it may be advantageous to select cognate RNA pol III promoters, e.g., avian, fish, etc. promoters.

One reason RNA Pol III promoters are especially desirable for expression of small engineered RNA transcripts is that RNA Pol III termination occurs efficiently and precisely at a short run of thymine residues in the DNA coding strand, without other protein factors, $T_4$ and $T_5$ being the shortest Pol III termination signals in yeast and mammals, with oligo (dT) terminators longer than $T_5$ being very rare in mammals. Accordingly, the multiple polymerase III promoter expression constructs of the invention will include an appropriate oligo (dT) termination signal, i.e., a sequence of 4, 5, 6 or more Ts, operably linked 3' to each RNA Pol III promoter in the DNA coding strand. A DNA sequence encoding an engineered RNA, e.g., and RNA effector molecule, e.g., a dsRNA hairpin or RNA stem-loop structure to be transcribed, may then be inserted between the Pol III promoter and the termination signal.

In order to isolate the DNA corresponding to these promoter elements, it is customary to obtain cloned copies of said sequence in the form of plasmids, from DNA repositories such as ATCC, or commercial sources. Alternatively, it is also customary and expedient to use the polymerase chain reaction (PCR) to generate multiple copies of the promoters by using only a small segment of sequence to design "PCR primers" and enzymatically amplify and physically isolate a substantially pure solution of each promoter. With the application of specific restriction enzymes and the appropriate design of said primers, it is customary to insert (recombine) these promoter elements to become part of the plasmid vector. One skilled in the art will appreciate that during the implementation of a strategy for inserting the promoters into the DNA backbone plasmids, provisions will typically be made to precisely insert further elements of interest. In the case of this invention, those elements constitute short stretches of DNA (preferably less than 50, 60, 70, 80, or 100 base pairs in length), prepared through PCR or by synthetic DNA polymerization methods or a combination of the two, and will encode the RNA effector molecule(s) of interest, e.g., in some aspects shRNA sequences which include complementary stretches of about 19 to 29 nucleotides (about 18, 19, 20, 21, 22, 23, 24, 25, 26, 27, 28, or 29 nucleotides) capable of hybridizing to form a dsRNA sequence ("stem") of about 19 to about 29 bp substantially identical and complementary to a region of a target nucleic acid to be inhibited, e.g., a DNA or RNA molecule produced by a cell, virus or pathogen. Cloning of promoter elements may also involve the introduction of restriction sites or other short sequences interposed between the canonical promoter sequence and the sequences encoding the RNA molecule to be expressed. Such elements are capable of modifying the function of the promoter and/or the expressed RNA and may constitute novel promoter sequences if function is maintained or enhanced. For example, the 7SK promoter sequence in FIG. 4(e) demonstrates enhanced function with respect to the FIG. 4(a) 7SK element (7SK 256) with the insertion of a 4 nucleotide extension 3' of the restriction site relative to the FIG. 4(a) promoter. This particular 7SK variant promoter sequence utilizes four inserted A residues, but four G residues could be used as an alternative.

Upon assembly of the recombinant DNA plasmid, bacteria are used as "factories" to produce large quantities of the final vector. The E. coli bacterium is frequently used for plasmid fermentation, and it may be advantageous to employ for this purpose E. coli strains having a reduced genome as described in, e.g., Blattner et al., Published U.S. Patent Application No. 2005/0032225, the teaching of which is incorporated herein by reference. The vector manufactured in this manner, isolated and purified according to methods known in the art, can be introduced into living cells with a variety of methods, collectively known as "transfection". Once inside the cell, the promoter elements are recognized by the cellular machinery available for gene transcription and the RNA effector molecules, e.g., shRNAs, will be produced.

Other bacterial strains that may be advantageous for propagating a plasmid expression vector of the invention include the E. coli GT 16 Competent Cells available commercially from InvivoGen, San Diego, Calif. GT116 is a sbcCD deletion strain specifically engineered to support the growth of plasmid DNAs carrying hairpin structures, such as the plasmids of the invention engineered to express one or more RNA effector molecules which are hairpin RNAs. Hairpin structures are known to be unstable in E. coli due to their elimination by a protein complex called SbcCD that recognizes and cleaves hairpins (Connelly et al., Proc. Natl. Acad. Sci. USA 95:7969-74 (1998)). The sbcCD and sbcD genes are deleted in E. coli GT116, which improves its utility for cloning plasmids with hairpin or other palindrome-containing structures.

A variety of means, both chemical and physical, may be used to introduce the plasmid expression vectors into a cell or tissue or a living organism, and, as such, a composition comprising a plasmid expression vector in a pharmaceutically acceptable vehicle or formulation constitutes a pharmaceutical composition. For the preparation of plasmid DNA as a pharmaceutical composition, such methods include formulations with cationic amphiphilic local anesthetics such as bupivacaine, positively charged nucleic acid binding agents such as polyamines (e.g. spermine) or a number of liposomal or lipid-containing agents which promote DNA update through cell membranes. Other components of a pharmaceutical composition comprising these expression vectors will include agents such as buffers and stabilizers to ensure chemical stability and solubility of the DNA vector in a homogenous solution suitable for pharmaceutical administration.

RNA pol III promoter vectors encode RNA molecules (which can have one or more introns or no introns and can have a polyA tail or no polyA tail) that are made in the nucleus and are primarily retained in the nucleus. These nuclear dsRNA effector molecules may be used to induce transcriptional gene silencing (TGS). However, a percentage of the transcribed dsRNAs reaches the cytoplasm and can therefore induce post transcriptional gene silencing (PTGS). For TGS induction, the dsRNA desirably contains a promoter sequence, a subset of a promoter sequence, a promoter sequence/transcription initiation site sequence, or another regulatory region sequence (optionally in combination with a sequence operably linked to such promoter/regulatory region in the DNA or RNA target as described below), and is retained in the nucleus. Alternatively, the dsRNAs may contain only coding and/or 3' and/or 5' UTR sequence, or may desirably contain a combination of coding and/or UTR sequence and/or promoter sequence. Such "fusion target" dsRNAs may contain, e.g., dsRNAs encoding both a promoter sequence and a linked gene sequence to be targeted for concurrent TGS and PTGS. The RNA pol III expression constructs of the invention, designed to deliver multiple short hairpin dsRNAs, are ideally suited to delivery of one or more dsRNAs targeting promoter and/or other regulatory sequences as well as one or more dsRNAs targeting coding regions and/or 3' UTRs and/or 5' UTRs. Also, including one or more promoters as taught in PCT/US2004/026999 (WO2005/040388) to create multiple-compartment expression systems of the invention can ensure that such a "fusion target" sequence is expressed in all of the relevant compartments, e.g., cytoplasm, nucleus, and nucleolus, by use of the requisite compartment-specific promoters to initiate transcription. For PTGS, the dsRNA contains sequence derived from an RNA (e.g., coding or UTR sequence from an mRNA) and does not have to contain promoter sequence. In addition, more efficient PTGS is induced by including promoters that enable cytoplasmic transcription (e.g., mitochondrial promoters) or by vectors that result in more efficiently cytoplasmically transported RNA, e.g., by inclusion of a CTE (constitutive transport element), such as the CTE of the Mason-Pfizer Monkey Virus or another simian retroviral transport element, see, e.g., U.S. Pat. Nos. 5,585, 263 and 5,880,276. If desired, PTGS and TGS can be induced simultaneously with a combination of these vectors using the methods described herein and techniques known to those skilled in the art.

Other expression control sequences include appropriate transcription initiation, termination (e.g., a sequence of 4 or 5 Ts as a polymerase III terminator), promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product.

It will be recognized that any of the vectors described herein or any other standard vector can be used to generate any of the desired biologically active nucleic acid structures of the invention, e.g., dsRNAs, including microRNAs, mRNA (translated if desired, into polypeptide), antisense RNA, and ribozymal RNA, and used in the present methods.

Methods for Enhancing Post-Transcriptional Gene Silencing

To enhance PTGS by dsRNA transcribed in the nucleus by RNA pol II, one or more introns and/or a polyadenylation signal can be added to the dsRNA to enable processing of the transcribed RNA. This processing is desirable because both splicing and polyadenylation facilitate export from the nucleus to the cytoplasm. In addition, polyadenylation stabilizes RNA pol II transcripts. These same strategies will be useful for expression of functional mRNAs that will be translated into protein. In some embodiments, a prokaryotic antibiotic resistance gene, e.g., a zeomycin expression cassette, is located in the intron. Other exemplary prokaryotic selectable markers include other antibiotic resistance genes such as kanamycin, including the chimeric kanamycin resistance gene of U.S. Pat. No. 5,851,804, aminoglycosides, tetracycline, and ampicillin. The zeomycin gene is under the regulatory control of a prokaryotic promoter, and translation of zeomycin in the host bacterium is ensured by the presence of Shine-Dalgarno sequences located within about 10 base-pairs upstream of the initiating ATG. Alternatively, the zeomycin expression cassette can be placed in any location between the inverted repeat sequences of the hairpin (i.e., between the sense and antisense sequences with substantial identity to the target nucleic acid to be silenced).

Although inverted repeat sequences are usually deleted from DNA by DNA recombination when a vector is propagated in bacteria, a small percentage of bacteria may have mutations in the recombination pathway that allow the bacteria to stably maintain DNA bearing inverted repeats. In order to screen for these infrequent bacteria, a zeomycin selection is added to the culture. The undesired bacteria that are capable of eliminating inverted repeats are killed because the zeomycin expression cassette is also deleted during recombination. Only the desired bacteria with an intact zeomycin expression cassette survive the selection.

After the DNA is isolated from the selected bacteria and inserted into eukaryotes (e.g., mammalian cell culture) or into animals (e.g., mammals) for expression of RNA, the intron is spliced from the RNA transcripts. If the zeomycin expression cassette is located in the intron, this cassette is removed by RNA splicing. In the event of inefficient splicing, the zeomycin expression cassette is not expressed because there are no eukaryotic signals for transcription and translation of this gene. The elimination of the antibiotic resistance cassette is desirable for applications involving short dsRNA molecules because the removal of the cassette decreases the size of the dsRNA molecules. The zeomycin cassette can also be located beside either end of an intron instead of within the intron. In this case, the zeomycin expression cassette remains after the intron is spliced and can be used to participate in the loop structure of the hairpin. These RNA pol II transcripts are made in the nucleus and transported to the cytoplasm where they can effect PTGS. However, some RNA molecules may be retained in the nucleus. These nuclear RNA molecules may effect TGS. For TGS applications, the encoded dsRNA desirably contains a promoter sequence or a subset of a promoter sequence, desirably including promoter/transcription initiation site sequences. In order to more efficiently retain RNA within the nucleus, the intron and/or polyadenylation signal can be removed.

Another strategy for both cytoplasmic and nuclear localization is to use "upstream" or internal RNA pol III promoters (see, e.g., Gene regulation: A Eukaryotic Perspective, 3$^{rd}$ ed., David Latchman (Ed.) Stanley Thornes Cheltenham, UK, 1998). These promoters result in nuclear transcribed RNA transcripts, some of which are exported and some of which are retained in the nucleus and hence can be used for PTGS and/or TGS. These promoters can be used to generate hairpins, including the partial and forced hairpin structures as described in WO 2004/011624, published 5 Feb. 2004, or duplex RNA through the use of converging promoters or through the use of a two vector or two cistronic system. One promoter directs synthesis of the sense strand, and the other promoter directs synthesis of the antisense RNA, usually from two different copies of a gene sequence. The length of RNA transcribed by these promoters is generally limited to several hundred nucleotides (e.g., 250-500). In addition, transcriptional termination signals may be used in these vectors to enable efficient transcription termination.

Much of the nomenclature and general laboratory procedures required in this application can be found in Sambrook J. et al., *Molecular Cloning: A Laboratory Manual* (3rd Ed.), Vol. 1-3, Cold Spring Harbor Laboratory, Cold Spring Harbor, N.Y., 2000. The manual is hereinafter referred to as "Sambrook et al."

Standard techniques for cloning, DNA isolation, amplification and purification, for enzymatic reactions involving DNA ligase, DNA polymerase, restriction endonucleases and the like, and various separation techniques are those known and commonly employed by those skilled in the art of molecular biology, as e.g., in the following reference texts, incorporated herein by reference: A number of standard techniques are described in Ausubel et al. (1994) *Current Protocols in Molecular Biology*, Green Publishing, Inc., and Wiley and Sons, New York, N.Y.; Sambrook et al. (above); Maniatis et al. (1982) Molecular Cloning, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering Principles and Methods, Vols.* 14, Plenum Press, New York. A particularly useful technique employed herein, called "chain reaction cloning", is described in U.S. Pat. No. 6,143,527, "Chain reaction cloning using a bridging oligonucleotide and DNA ligase", Pachuk et al. *Abbreviations and nomenclature*, where employed, are deemed standard in the field and commonly used in professional journals such as those cited herein.

Pharmaceutical Compositions

The multiple RNA polymerase III promoter expression systems of the invention may advantageously be used for a variety of pharmaceutical applications as described elsewhere herein. In various embodiments, the pharmaceutical composition includes about 1 ng to about 20 mg of nucleic acid, e.g., RNA, DNA, plasmids, viral vectors, recombinant viruses, or mixtures thereof, which provide the desired amounts of the nucleic acid molecules (dsRNA homologous and complementary to a target nucleic acid, mRNAs, microRNAs, antisense RNA, triplex-forming RNA, etc.). In some embodiments, the composition contains about 10 ng to about 10 mg of nucleic acid, about 0.1 mg to about 500 mg, about 1 mg to about 350 mg, about 25 mg to about 250 mg, or about 100 mg of nucleic acid. Those of skill in the art of clinical pharmacology can readily arrive at such dosing schedules using routine experimentation.

Suitable carriers include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous (IV), intra-arterial, intramuscular (IM), subcutaneous (SC), intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g., mammalian, including human, canine, feline, bovine, equine, porcine) subjects in the form of liquids, including sterile, non-pyrogenic liquids for injection, emulsions, powders, aerosols, tablets, capsules, enteric coated tablets, or suppositories.

A pharmaceutical composition can be prepared as described herein, e.g., comprising a DNA plasmid construct expressing, under the control of two, three, four or more RNA polymerase III promoters, two, three, four or more short hairpin dsRNA molecules substantially homologous to, e.g., sequences from one or more genes of a target pathogen, e.g., a virus, such as HBV, HCV, HIV, HPV, the smallpox virus, or a sequence associated with another pathogen or other nucleic acid sequence of human, veterinary, or agricultural interest, e.g., the human cell receptor sequences for the Anthrax toxin, or other gene sequences associated with mammalian, vertebrate, or invertebrate diseases or disorders, e.g., Huntington's Disease, or VEGF, associated with macular degeneration, or avian influenza or West Nile Virus sequences engineered for treatment in human, equine, or avian host cells. The expression construct may include additional promoter sequences, e.g., the bacteriophage T7 promoter, in which case it may be necessary to co-deliver or co-express the cognate polymerase. E.g., the T7 RNA polymerase can be co-delivered and expressed from the same or another plasmid under the control of a suitable promoter, e.g., an RNA polymerase II promoter such as hCMV, simian CMV, or SV40. In some embodiments, the same or another construct expresses the target gene (e.g., a target smallpox gene) contemporaneously with the dsRNA(s) homologous to the target smallpox gene. The pharmaceutical composition is prepared in a pharmaceutical vehicle suitable for the particular route of administration. For IM, SC, IV, intraperitoneal, intradermal, intrathecal or other parenteral routes of administration, a sterile, non-toxic, pyrogen-free aqueous solution such as Sterile Water for Injection, and, optionally, various concentrations of salts, e.g., NaCl, and/or dextrose (e.g., Sodium Chloride Injection, Ringer's Injection, Dextrose Injection, Dextrose and Sodium Chloride Injection, and/or Lactated Ringer's Injection) is commonly used. Optionally, other pharmaceutically appropriate additives, preservatives, or buffering agents known to those in the art of pharmaceutics are also used. If provided in a single dose vial for injection, the dose will vary as determined by those of skill in the art of pharmacology, but may typically contain between 5 mcg to 500 mcg of the active construct. If deemed necessary, significantly larger doses may be administered without toxicity, e.g., up to 5-10 mg.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the expression construct(s) with suitable non-irritating excipients or carriers such as cocoa butter, polyethylene glycol, or a suppository wax which are solid at ambient temperature but liquid at body temperature and therefore melt in the rectum or vaginal cavity and release the microparticles.

Solid dosage forms for oral administration include capsules, tablets, pills, powders, and granules. In such solid dosage forms, the expression construct(s) are mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Dosage forms for topical or transdermal administration of an inventive pharmaceutical composition include ointments, pastes, creams, lotions, gels, powders, solutions, sprays, inhalants, or patches. The expression construct(s) are admixed under sterile conditions with a pharmaceutically acceptable carrier and any needed preservatives or buffers as may be required. Ophthalmic formulation, eardrops, and eye drops are also contemplated as being within the scope of this invention.

Transdermal patches have the added advantage of providing controlled delivery of a compound to the body. Such dosage forms can be made by dissolving or dispensing the expression construct(s) in a proper medium. Absorption enhancers can also be used to increase the flux of the compound across the skin. The rate can be controlled by either providing a rate controlling membrane or by dispersing the expression construct(s) in a polymer matrix or gel.

Desirable Methods of Administration of Expression Constructs

The DNA and/or RNA constructs of the invention may be administered to the host cell/tissue/organism as "naked" DNA, RNA, or DNA/RNA, formulated in a pharmaceutical vehicle without any transfection promoting agent. More efficient delivery may be achieved as known to those of skill in the art of DNA and RNA delivery, using e.g., such polynucleotide transfection facilitating agents known to those of skill in the art of RNA and/or DNA delivery. The following are exemplary agents: cationic amphiphiles including local anesthetics such as bupivacaine, cationic lipids, liposomes, or lipidic particles; polycations such as polylysine; branched, three-dimensional polycations such as dendrimers; carbohydrates; detergents; or surfactants, including benzylammonium surfactants such as benzylkonium chloride. Non-exclusive examples of such facilitating agents or co-agents useful in this invention are described in U.S. Pat. Nos. 5,593,972; 5,703,055; 5,739,118; 5,837,533; 5,962,482; 6,127,170; and 6,379,965, as well as International Patent Application Nos. WO03/093449, published 13 Nov. 2003 (multifunctional molecular complexes and oil/water cationic amphiphile emulsions), and WO99/21591, published 6 May 1999 ("Compositions and Methods for Delivery of Genetic Material"); the teaching of which is hereby incorporated by reference. U.S. Pat. Nos. 5,824,538; 5,643,771; and 5,877,159 (incorporated herein by reference) teach delivery of a composition other than a polynucleotide composition, e.g., a transfected donor cell or a bacterium containing the expression constructs of the invention.

In some embodiments, the expression construct(s) of the invention is complexed with one or more cationic lipids or cationic amphiphiles, such as the compositions disclosed in U.S. Pat. No. 4,897,355 (Eppstein et al., filed Oct. 29, 1987); U.S. Pat. No. 5,264,618 (Felgner et al., filed Apr. 16, 1991); or U.S. Pat. No. 5,459,127 (Felgner et al., filed Sep. 16, 1993). In other embodiments, the expression construct(s) is complexed with a liposome/liposomic composition that includes a cationic lipid and optionally includes another component, such as a neutral lipid (see, for example, U.S. Pat. No. 5,279,833 (Rose); U.S. Pat. No. 5,283,185 (Epand); and U.S. Pat. No. 5,932,241 (Gorman)). In other embodiments, the expression construct(s) are complexed with the multifunctional molecular complexes of U.S. Pat. Nos. 5,837,533; 6,127,170; and 6,379,965 (Boutin), or, desirably, the multifunctional molecular complexes or oil/water cationic amphiphile emulsions of U.S. Provisional Application Ser. No. 60/378,191, filed May 6, 2002, (WO03/093449, published 13 Nov. 2003, Satishchandran), the teaching of which is incorporated herein by reference. The latter application teaches a composition that includes a nucleic acid, an endosomolytic spermine that includes a cholesterol or fatty acid, and a targeting spermine that includes a ligand for a cell surface molecule. The ratio of positive to negative charge of the composition is between 01 to 2.0, preferably 0.5 and 1.5, inclusive; the endosomolytic spermine constitutes at least 20% of the spermine-containing molecules in the composition; and the targeting spermine constitutes at least 10% of the spermine-containing molecules in the composition. Desirably, the ratio of positive to negative charge is between 0.8 and 1.2, inclusive, such as between 0.8 and 0.9, inclusive. The targeting spermine is designed to localize the composition to a particular cell or tissue of interest. The endosomolytic spermine disrupts the endosomal vesicle and encapsulates the composition during endocytosis, facilitating release of the nucleic acid from the endosomal vesicle and into the cytoplasm or nucleus of the cell. Use of such a mixture of targeting spermine/endosomolytic spermine achieves not only transfection, but enhances expression as well.

A DNA expression vector of the invention may be complexed as taught in WO03/093449, published 13 Nov. 2003, with a mixture of 35% mannosyl spermine to 65% cholesteryl spermine to achieve targeted transfection of immune cells, e.g., macrophages, via the mannose receptor, when administered IV in mice. Targeted transfection of hepatocytes in vivo for delivery of dsRNAs against HBV and/or HCV may be accomplished through IV injection with a composition comprising a DNA or RNA expression vector as described herein complexed with a mixture (e.g., a 35%/65% ratio) of a lactosyl spermine (mono or trilactosylated) and cholesteryl spermine (containing spermine to DNA at a charge ratio of 0.8). Such compositions are especially useful for pharmaceutical applications and may readily be formulated in a suitable sterile, non-pyrogenic vehicle, e.g., buffered saline for injection, for parenteral administration, e.g., IV (including IV infusion), 1M, SC, and for intraperitoneal administration, as well as for aerosolized formulations for pulmonary delivery via inhalation. In certain formulations, a DNA expression construct of the invention may be complexed with an endosomolytic spermine such cholesteryl spermine alone, without a targeting spermine; some routes of administration, such as intraperitoneal injection or infusion, may achieve effective hepatic delivery and transfection of a DNA construct of the invention, and expression of RNA effector molecules, e.g., multiple dsRNA hairpins effective against HBV and/or HCV.

A DNA expression vector of the invention may also be formulated as a microemulsion for in vivo oral or parenteral, e.g., intravenous delivery, as taught in WO03/093449, published 13 Nov. 2003, the teaching of which is hereby incorporated by reference. Formulations desirably contain amphiphiles such as the local anaesthetic bupivacaine, cholesteryl spermine, benzalkonium chloride, or octyl spermine. In vivo experiments in mice suggest that oral administration results in significant delivery to the liver. Intravenous administration of microemulsions results in transfection of organs with large capillary beds, e.g., lung, liver, spleen, and kidney.

In yet other embodiments, the expression construct(s) is complexed with any other composition that is devised by one of ordinary skill in the fields of pharmaceutics and molecular biology. In some embodiments, the construct or vector is not complexed with a cationic lipid.

Transformation/transfection of the cell may occur through a variety of means including, but not limited to, lipofection, DEAE-dextran-mediated transfection, microinjection, protoplast fusion, calcium phosphate precipitation, viral or retroviral delivery, electroporation, or biolistic transformation. The expression construct (DNA) may be naked DNA or local anesthetic complexed DNA (Pachuk et al., *Biochim. Biophys. Acta* 1468:20-30 (2000)). Desirably the eukaryotic cell, e.g., vertebrate (e.g., mammalian), is in vivo or is a cell that has been cultured for only a small number of passages (e.g., less than 30 passages of a cell line that has been directly obtained from ATCC), or are primary cells.

Desirable Cells

In still further embodiments of any aspect of the invention, the cell is a eukaryotic plant cell or an animal cell. Desirably, the animal cell is an invertebrate or vertebrate cell (e.g., a mammalian cell, for example, a human cell). The cell may be ex vivo or in vivo. The cell may be differentiated or undifferentiated, a gamete, an embryonic cell, including an embryonic stem cell, a somatic cell, for example, a cancer cell, an adult or somatic stem cell, a cell of the immune system, a neuronal cell, a muscle cell, including a smooth muscle or cardiac muscle cell, a hormone-producing cell, a blood cell, a liver cell, an adipocyte, etc. In some embodiments, one or more proteins involved in gene silencing, such as Dicer or Argonaut, are overexpressed or activated in the cell or animal to increase the amount of inhibition of gene expression.

Inclusion of a Mammalian Origin of Replication

While ordinarily not considered desirable for human pharmaceutical applications, a human or mammalian origin of replication may be included in expression constructs of the invention intended for other applications, e.g., non-clinical research. An origin of replication enables the DNA plasmid to be replicated upon nuclear localization and thus enhances expression, both level and duration of expression. The advantage is that more plasmid is available for nuclear transcription and therefore more effector molecules are made (e.g., more antisense, mRNA, dsRNA hairpins, microRNAs and/or more dsRNA duplexes). Many origins are species-specific and work in several mammalian species but not in all species. For example, the SV40 T origin of replication (e.g., from plasmid pDsRed1-Mito from Clontech; U.S. Pat. No. 5,624,820) is functional in mice but not in humans. This origin can thus be used for vectors that are used or studied in mice. Other origins that can be used for human applications are those such as, for example, the Epstein-Barr nuclear antigen (EBNA) origin (e.g., plasmids pSES.Tk and pSES.B from Qiagen). DNA vectors containing these elements are commercially available, and the DNA segment encoding the origin can be obtained using standard methods by isolating the restriction fragment containing the origin or by PCR amplifying the origin. The restriction maps and sequences of these vectors are available publicly and enable one skilled in the art to amplify these sequences or isolate the appropriate restriction fragment. These vectors replicate in the nuclei of cells that express the appropriate accessory factors such as SV40 TAg and EBNA. The expression of these factors is easily accomplished because some of the commercially available vectors (e.g., pSES.Tk and pSES.B from Qiagen) that contain the corresponding origin of replication also express either SV40 Tag or the EBNA. These DNA molecules containing the origin of replication can be easily cloned into a vector of interest (e.g., a vector expressing a dsRNA such as a hairpin or duplex) by one skilled in the art. These vectors are then co-transfected, injected, or administered with a vector expressing EBNA or Tag to enable replication of the plasmid bearing the EBNA or Tag origin of replication, respectively. Alternatively, the genes encoding EBNA or Tag are cloned into any another expression vector designed to work in the cells, animal, or organism of interest using standard methods. The genes encoding EBNA and Tag can also be cloned into the same vector bearing the origin of replication. Suitable origins of replication are not limited to Tag and EBNA; for example, REPLICor Inc. (Montreal, Quebec) has identified a 36 base-pair mammalian origin consensus sequence that permits the DNA sequence to which it is attached to replicate (as reviewed in *BioWorld Today*, Aug. 16, 1999, Volume 10, No. 157). This sequence does not need the co-expression of auxiliary sequences to enable replication.

Also included within the scope of the invention are kits comprising compositions containing the expression constructs of the invention; such kits may include expression vectors comprising multiple Pol III promoters and designed for ready insertion of sequences encoding RNA effector molecules to be transcribed, or designed for ready insertion of multiple Pol III promoter-driven expression cassettes, e.g., through placement within the expression vector of appropriately chosen restriction sites, and may also optionally comprise media, solutions, and other compositions to assist in the stability, delivery, ease of use, or efficacy of the expression constructs.

Treatment of Hepatitis B Disease Using Expression Vectors Comprising Multiple RNA Polymerase III Promoters Encoding Multiple dsRNA Hairpins Viral hepatitis constitutes a major world health problem for which adequate treatment is not yet available. A vaccine is available as prophylaxis against human hepatitis B, but not against human hepatitis C, and infection with either hepatitis B or C virus, e.g., human hepatitis B virus (HBV) or human hepatitis C virus (HCV) frequently results in chronic viral hepatic disease.

Drug therapy against hepatitis C, including ribavirin and interferon, is only partially effective. It is estimated that 75-85% of infected persons will develop a chronic infection, with 70% of chronically infected persons expected to develop chronic liver disease including hepatocellular carcinoma. Chronic HCV related liver disease is a leading indication for liver transplant.

Although a human hepatitis B vaccine has been available since 1982, it is estimated that 350 million persons worldwide are chronically infected with HBV. While the number of new infections per year in the United States has declined from an average of 260,000 in the 1980s to about 78,000 in 2001, there are an estimated 1.25 million hepatitis B carriers, defined as persons positive for hepatitis B surface antigen (HBsAg) for more than 6 months. Such carriers of HBV are at increased risk for developing cirrhosis, hepatic decompensation, and hepatocellular carcinoma. Although most carriers do not develop hepatic complications from chronic hepatitis B, 15% to 40% will develop serious sequelae during their lifetime, and death from chronic liver disease occurs in 15-25% of chronically infected persons. Thus, there is a pressing need for improved therapeutic agents effective in patients suffering from HBV and/or HCV infection, especially chronic infection, which together are estimated to account for 75% of all cases of liver disease around the world. There is also an extreme need for prophylactic methods and agents effective against HCV.

While HBV and HCV are very desirable viral targets for dsRNA-based therapies (RNAi), the variability and mutability of the viruses and the high rates of transcription of the viruses make HBV and HCV very challenging targets for any therapeutic and/or prophylactic approach. In order to knock down viral genome replication using RNAi there is a need to identify conserved and unique regions in the viral genome. At that same time, it is very important in order to avoid toxicity that any sequences selected for gene silencing be absent from the human genome. Conserved HBV and HCV sequences suitable for use as dsRNA hairpins expressed by the multiple polymerase III promoter constructs of the invention are taught in WO2005/014806, published 17 Feb. 2005, and in U.S. Provisional Application Ser. No. 60/638,294, filed 22

Dec. 2004, "Conserved HBV and HCV Sequences Useful for Gene Silencing", the teaching of which is hereby incorporated by reference.

Although various small molecule drugs exist such as which inhibit the replication enzymes of these viruses, the disease cannot generally be cured, usually only temporarily abated, by these agents because 1) the agents do not destroy the viral nucleic acid genomes which can continue to replicate and/or produce viral proteins, and 2) the agents are rendered ineffective over time because the viral genome mutates and produces variant replication enzymes that are resistant to the inhibitors.

HBV belongs to the family of hepadnaviruses. The HBV genome is a relaxed circular, partially double stranded DNA of approximately 3,200 base pairs. There are 4 partially overlapping open reading frames encoding the envelope (pre-S/S), core (precore/core), polymerase, and X proteins. The pre-S/S open reading frames encode the large (L), middle (M), and small (S) surface glycoproteins. The precore/core open reading frame is translated into a precore polypeptide, which is modified into a soluble protein, the hepatitis B e antigen (HBeAg) and the nucleocapsid protein, hepatitis B core antigen. Mutations in the core promoter and precore region have been shown to decrease or abolish HBeAg production. The polymerase protein functions as a reverse transcriptase as well as a DNA polymerase. The X protein is a potent trans-activator and may play a role in hepatocarcinogenesis.

The replication cycle of HBV begins with the attachment of the virion to the hepatocyte. Inside the hepatocyte nucleus, synthesis of the plus strand HBV DNA is completed and the viral genome is converted into a covalently closed circular DNA (cccDNA). Most antiviral agents that have been examined so far have little or no effect on cccDNA, which accounts for the rapid reappearance of serum HBV DNA after cessation of antiviral therapy. The aims of treatment of chronic hepatitis B are to achieve sustained suppression of HBV replication and/or expression of HBV antigens and remission of liver disease.

The multiple polymerase III expression vectors of this invention, when delivered to a virally infected cell, have the unique ability to destroy the viral nucleic acid products directly. Moreover, inherent and integral to the design and intent of these multiple promoter vectors (which express a plurality of different inhibitory short hairpin dsRNAs targeting different portions of the viral genome), is the property of generating multiple different viral antagonists simultaneously. The antagonists (shRNAs) target different genome sequences in the viral genome. One of these antagonists would probably be sufficient to disable the virus, however the redundancy serves as a "backup" mechanism such that if the viral sequence mutates to render one antagonist inert, there are 2, 3, 4 or more additional antagonists available. Additionally, by targeting multiple sites in the viral genome, different DNA or RNA products of the virus which play different roles in the disease pathology can be attacked at the same time.

In the case of Hepatitis B for example, in one embodiment, the instant invention uses 4, 5, or more shRNA molecules (e.g., named "799", "1907", "2791", "1737", "1991", "1943" as set forth in FIG. 5) comprising highly conserved HBV sequences as taught in U.S. Provisional Application Ser. No. 60/638,294, filed 22 Dec. 2004. Other of the conserved HBV sequences disclosed therein, including sequences of e.g., 19 to 29 nucleotides, which comprise all or part of "799", "1907", "2791", "1737", "1991", or "1943", may be selected for inclusion in a dsRNA hairpin to be expressed by the multiple polymerase III expression vectors of the invention. Due to the nature of HBV gene expression and overlapping transcriptional products this allows targeting of multiple RNA transcripts as well as the replicative template of the virus which will interfere with replication and expression of more than one of the viral proteins. One of the shRNA molecules, "1737", uniquely can disable the RNA encoding a product known as the X protein (HbX). Strong evidence exists in the biomedical literature that the X protein plays a role in establishment and/or maintenance of liver cancer. Because the existing drugs that can to some extent inhibit viral replication cannot eliminate the cell of integrated or other residual copies or portions of the viral genome, these drugs cannot shut off the production of HbX, even in patients "cured" of infectious HBV, and thus can not directly reduce any incidence of cancer that is mediated by dormant HbX. Multiple anti-HBV dsRNA hairpin expression constructs of the present invention can attack both the replication of the virus and the expression of all viral proteins, some which cause the inflammatory insult which results in hepatitis, and others such as HbX, which are believed to promote hepatocellular carcinoma via a distinct but not fully understood mechanism. It is recognized that the principles taught herein can be used to design constructs of the invention specifically tailored to treat such "post infection" patients, which express dsRNAs against Hbx and any other residual HBV antigens.

EXAMPLES

The present invention is further defined in the following Examples. It should be understood that these Examples, while indicating preferred embodiments of the invention, are given by way of illustration only. From the above discussion and these Examples, one skilled in the art can ascertain the preferred features of this invention, and without departing from the spirit and scope thereof, can make various changes and modifications of the invention to adapt it to various uses and conditions.

Construction and Description of Multiple Pol III Promoter Expression Vectors

Using standard recombinant DNA techniques, a plasmid containing a bacterial antibiotic selection marker and origin of replication was selected as the starting point for the insertion of the specific promoter/shRNA combinations below. The plasmid was made by first combining an approximately 1 kb fragment (containing the bacterial origin of replication, between the ampicillin resistance gene and the multiple cloning site) of the widely available pUC18 vector (Yanisch-Perron et al., Gene 33:103-19 (1985), erratum in Gene 114: 81-83 (1992)) with a chimeric kanamycin resistance gene as disclosed in U.S. Pat. No. 5,851,804. A variety of commercially-available plasmid vectors obtainable from suppliers such as Invitrogen, Clontech, Stratagene and others may be used as an alternative source of vector elements, or to substitute for Applicants' vector for use as starting material to produce functionally equivalent variants of the vectors described below. The methods used to assemble the vector from source sequences include restriction enzyme digestion, gel electrophoresis, PCR (polymerase chain reaction), DNA sequencing, enzymatic ligation, and "chain reaction cloning", as described in U.S. Pat. No. 6,143,527, "Chain reaction cloning using a bridging oligonucleotide and DNA ligase", Pachuk et al., and other methods common and well known to those skilled in the art.

The Applicants found it expedient to prepare single Pol III promoter vector constructs prior to generating the multiple promoter constructs. A basic single-promoter RNA pol III vector for expressing single short hairpin RNAs (shRNA) was generated by enzymatic joining of the origin-of-replication restriction fragment above (ori) to the chimeric kanamycin resistance gene, and then to a desired Pol III promoter/shRNA expression cassette in sequential steps. The promoter/shRNA expression cassettes were made by joining the promoter with short fragments (approximately 50 to 60 bp) comprising the shRNA sequence of interest, made as synthetic, double-stranded oligonucleotides by custom order from a commercial vendor. The purpose of constructing single-promoter vectors as precursors to multiple promoter vectors embodies several beneficial aspects. First, it allows for the functional confirmation of each promoter/shRNA pair in the absence of other Pol III expression elements or shRNAs which could confound the means of detection of the object promoter/shRNA pair or elements. Second, it allows for DNA sequencing of all or part of each cassette using sequencing primers which otherwise would have multiple annealing sites in multiple promoter vectors, and render sequencing in that context impossible. Third, the verified single-promoter cassettes can be efficiently mobilized for cloning into any number of incipient multiple-promoter vectors by the intentional design of cloning restriction site pairs which are unique for each promoter element.

Following the determination of adequate expression levels and gene silencing effects of the single-promoter vectors, multiple-promoter vectors were constructed from the single-promoter vector promoter/shRNA cassettes in a stepwise fashion to contain, 2, 3, 4, or 5 Pol III promoters each driving the expression of a different shRNA. Thus, an effective single-promoter construct expressing a shRNA was modified to add a second promoter-shRNA cassette. The positioning of the second cassette (see FIG. 8) relative to the first cassette was chosen empirically by generating several alternative 2-promoter forms of the two-promoter plasmid (varied by the relative positions of the $1^{st}$ and $2^{nd}$ cassette with respect to the other vector elements, and varied by the orientation of each cassette with respect to direction of transcription). It will be appreciated by one skilled in the art that, when attempting to combine 2 cassettes for optimal expression in a single vector, the position around the circular vector as well as the "backward" or "forward" transcriptional directionality of the cassette can be varied to produce as many as 8 different varieties, all containing the same elements. Moreover, when attempting the expression of 2 different shRNA elements from two different promoters in this vector, the different combinations of shRNA sequence with each of the two promoters would produce 16 different variants of said vector, again all containing the same elements, but in different arrangements. Applicants have observed that these different configurations can result in a significant variation in the apparent levels of expression of each shRNA. Nevertheless, the multiple polymerase III promoter constructs of the present invention demonstrate that an efficient selection of relatively optimized configurations of these elements for the purpose of expressing the multiple effector RNAs (particularly shRNA) for effective gene silencing effects can be accomplished without undue experimentation.

In the context of the present invention, it is desirable to produce at least 3, 4, 5, or more different RNA effector molecules (e.g., shRNA molecules) efficiently from one expression construct. The preceding description of a 2-promoter vector is therefore meant to provide a simple illustration of the combinatorial possibilities when engineering said constructs. Given that all permutations do not function equally well, and that producing a vector with over 3 shRNA cassettes would require testing of a large number of vector permutations if all possible permutations were to be evaluated systematically, applicants sought to establish a strategy, (protocol, formula, method, series of steps) which could be used pragmatically to obtain a mutiple-pol III promoter expression construct in which all shRNA elements are expressed in a manner robust enough for all elements to independently, as well as coordinately, effect gene silencing in a mammalian cell. The stepwise approach to adding promoter cassettes in an iterative manner, which involved generating only a fraction of the total possible permutations of a multiple-promoter vector, and which is illustrated further in the examples below, has been demonstrated by Applicants to be a reliable, reproducible and efficient method of achieving simultaneous robust expression of shRNAs from these multiple promoter vectors. This is in contrast to the general belief that combinations of multiple promoter elements in this degree would be untenable due to problems of transcriptional interference (among promoters), exacerbated by problems maintaining these plasmids in bacteria due to repeated elements among promoters and inverted repeat element in the shRNA sequences therein.

Selection of Pol III Promoters

Example 1

A Tricistronic RNA Polymerase III-Based Expression Construct for Production of shRNAs which Reduce Hepatitis B RNA Production and Replication A series of plasmids were constructed to express three different Hepatitis B targeting shRNAs under the independent control of 3 separate RNA polymerase III promoters. The U6 and 7SK promoter/shRNA cassettes were placed adjacent to each other in the multiple cloning site of the vector, while a distal cloning site (adjacent to the kanamycin resistance gene) was used for the third promoter sequence (either the second copy of the U6 promoter or the H1 promoter). The 5' end of each shRNA element was joined to the 3' end of each promoter using a convenient restriction site, e.g., Sal I or HindIII, engineered by introducing 6 nt between the 3' end of the promoter and the start of the shRNA sequence. The sequence for each of the promoter elements is given in FIG. 4. The three shRNA sequences placed in the tricistronic vector, identified as 2791, 1907 and 1737, derived from HBV conserved regions, are shown in FIG. 5. Each shRNA begins with 21 bp of HBV sequence followed by a 9-base loop element (AGAGAACTT), in turn followed by a 21 bp sequence which is the reverse complement of the first 21 bp. Each promoter cassette contains a stretch of 5 thymidine residues at the 3' end to serve as a transcription terminator. Thus, the predicted transcript which includes the dsRNA hairpin actually contains additional 5' and 3' sequences: a 5' leader consisting of 6 bases (e.g., the Sal I or Hind III or other chosen recognition sequence), followed by the dsRNA hairpin sequences, followed by a short 3' terminal U tract, usually two (1, 2, 3, or 4) U residues incorporated during transcription termination. The choice of a Sal I or Hind III site is a matter of convenience, and it will be recognized that any number of other restriction sites, preferably 6 or 8 cutters (e.g., Aat II, Acc65 I, Acl I, Afl II, Age I, Apa I, ApaL I, Asc I, Ase I, AsiS I, Avr II, BamH I, Bcl I, BfrB I, Bgl II, BmgB I, BseY I, BsiW I, BspD I, BspE I, BspH I, BsrB I, BsrG I, BssH II, BssS I, BstB I, BstZ17 I, Cla I, Dra I, Eag I, EcoR I, EcoR V, Fse I, Fsp I, Hind III, Hpa I, Kas I, Kpn I, Mfe I, Mlu I, Msc I, Nae I, Nar I, Nco I, Nde I, NgoM IV, Nhe I, Not I, Nru I, Nsi I, Pac I, PaeR7 I, Pme I, Pml I, Pst I, Pvu I, Pvu II, Sac I, Sac II, Sal I, Sbf I, Sca I, Sfo I, Sma I, SnaB I, Spe I, Sph I, Ssp I, Stu I, Swa I, Tli I, Xba I, Xho I, Xma I; preferably Avr I (CCTAGG), BamH I (GGATCC), EcoR I (GMTTC), Hind III (AAGCTT), Kpn I (GGTACC), Nde I (CATATG), Not I (GCGGCCGC), Pst I (CTGCAG), Sal I (GTCGAC), or Xba I (TCTAGA)), could be utilized instead, in which case, the dsRNA hairpin transcript will include a different 5' leader sequence. These differences in length and composition of 5' and 3' transcript sequences flanking the dsRNA hairpin did not appear to adversely affect the ability of the dsRNA hairpin to effect dsRNA-mediated silencing, which suggests that, unlike synthetic dsRNA duplexes, endogenously expressed dsRNA hairpin constructs are effective despite varying in a number of respects, e.g., length of dsRNA "stem" between about 19-29 bp, length and composition of single-stranded loop, presence or absence of additional short 5' and/or 3' sequences. While the target sequences were chosen expressly to represent those identical among a large number of different isolates (strains) of HBV, for reference purposes the shRNA sequences can be mapped back to HBV isolate AYW such that shRNA 2791 contains the 21 bp sequence beginning at position 2791 of isolate AYW (GenBank® Accession No. V01460), shRNA 1907 at position 1907 of the GenBank® reference sequence etc, except for shRNA 799, which includes the sequence beginning at position 779 and extending through 799. For selection of conserved HBV and HCV sequences, see e.g., WO2005/014806, published 17 Feb. 2005, and U.S. Provisional Application Ser. No. 60/638,294, filed 22 Dec. 2004, "Conserved HBV and HCV Sequences Useful for Gene Silencing". An HBV target sequence of preferably 19 to 29 nucleotides, e.g., 18, 19, 20, 21, 22, 23, 24, 25, 26, 27, 28, or 29 consecutive conserved nucleotides, may be selected for use in a dsRNA hairpin, expressed as taught herein. In Experiment 1 of this example, the plasmid vector contains one copy of the 7SK promoter and 2 copies of the U6 promoter. In Experiment 2, the vector uses 3 different RNA polymerase III promoters (the H1 promoter in addition to 7SK and U6). In both experiments, a further variant of each plasmid is used in which the orientation of the 7SK promoter is reversed. The examples herein have utilized the basic 7SK promoter (FIG. 4A); however, sequences of 2 variants of the 7SK promoter, termed 7SK-e and 7SK4A (FIGS. 4d and 4e, respectively) can be substituted where the 7SK promoter is indicated. Thus, the set of vectors used in this Example comprises 4 different plasmids and all 4 vectors have been tested for effectiveness in reducing HBV RNA expression in two experimental systems where HBV RNA is generated in transfected tissue culture cells. The first system employs an unrelated set of plasmid constructs which are used to produce synthetic HBV RNA molecules which are linked to an mRNA (fusion constructs) which encodes for the luciferase protein. The ability of the plasmid vectors under evaluation to reduce expression of the HBV RNA fusion constructs is assessed by measuring the amount of luciferase enzymatic activity generated in the transfected cells. In the second experimental system, an HBV replicon model, the plasmid vectors under evaluation are co-transfected with a cloned HBV. The ability of the plasmid vectors to inhibit HBV replication and function is assessed by measurement of HBV surface antigen (HBV sAg).

Evaluation of Vectors in Luciferase fusion assay. In order to evaluate the ability of each vector to suppress expression of HBV RNA sequences, human rhabdosarcoma (RD) cells were co-transfected with a series of vectors ("Luc-fusion" vectors) which encode HBV RNA segments appended to the 3' end of the complete coding sequence for luciferase enzyme. A method for preparation and use of these vectors in the fusion assay has been disclosed in WO2004/076629, published 10 Sep. 2004, "Methods and Constructs for Evaluation of RNAi Targets and Effector Molecules". There were 5 different luc-fusion vectors used in these experiments as follows. Luc-AYW contains the complete genomic sequence of the AYW strain of HBV, Luc is a negative control vector devoid of HBV sequences, and Luc-2791, Luc-1907 and Luc-1737 each are the luciferase gene fused with short (app. 200 bp) HBV segments containing the targets of shRNA sequences 2791, 1907 and 1737, respectively.

For co-transfection, cells were seeded into six-well plates such that they were between 80-90% confluency at the time of transfection. All transfections were performed using Lipofectamine™ polycationic lipid/neutral lipid liposome formulation (Invitrogen) according to the manufacturer's directions. In this experiment, cells were transfected with 200 ng of each Luc-fusion plasmid and 800 ng of the experimental plasmid. Forty-eight hours post-transfection, cells were harvested and lysed, and luciferase activity was determined using the Bright-Glo® Luciferase Assay System (Promega Inc., Madison, Wis.). Luciferase activity is expressed as Relative Light Units (RLU) divided by mg total protein.

Results of these experiments are given in FIG. 3. While all four forms of the shRNA tricistronic vectors showed a significant decrease in HBV RNA expression as is evident when comparing luciferase activity values produced by plasmids not containing HBV sequences vs. the HBV-luc fusion plasmid (Luc-awy), not all shRNA-promoter cassettes were functional in all promoter configurations of the vector. Only in eiRNA vector number 41 were all three shRNAs capable of silencing their cognate test sequences in the luciferase fusion construct. Note that in both the comparison of vector 40 with 50, and of 41 with 51, function of at least one promoter-shRNA cassette can be restored by inverting the orientation of the cassette; however, as is seen in vector 50, restoration of the 1737 shRNA function is then accompanied by loss of function of the 2791 shRNA. All possible permutations and combinations of vector elements did not need to be tested to achieve the successful product exemplified by vector 41: the goal was achieved by using 3 distinct promoters and varying the orientation of one or more of the cassettes in an iterative fashion until the desired result was achieved. It should also be noted in the result that these experiments were not done under conditions to evaluate the relative potency of each of the vector constructs; i.e., the inherent potency of each shRNA product and its rate of production was not considered. In fact, luciferase activity values are diminished to a similar extent by all vectors whether or not they expressed all 3 shRNA or only 2. Nevertheless, the instant invention wherein an antiviral therapeutic is rendered superior by incorporation of multiple nucleic acid target sequences (to circumvent escape mutants) is embodied to a much larger extent in vector 41 than in the other vectors shown.

Evaluation of vectors in HBV replicon model. In this series of experiments, Huh7 cells (derived from a human hepatocyte cell line) are co-transfected with pHBV2, an infectious molecular clone of HBV, along with the individual effector RNA constructs to be evaluated. The total DNA used for transfection was 2.5 µg, and consisted of 50 ng of pHBV2, a variable amount of test construct (as in FIG. 6) and an inert, "filler" DNA plasmid (pGL3, Promega Corp, Madison, Wis.) in variable amounts as to maintain 2.5 µg in all transfections. At 5 to 6 days after transfection, cell culture medium was harvested and amounts of HBV surface antigen (sAg) secreted into the medium were assayed using the Auszyme Monoclonal kit (manufactured by Abbott Laboratories, Inc). The quantitation of sAg is well accepted as an indirect measurement of viral replication as well as viral transcription in HBV infected cells. Two sets of experiments were performed, each involving multiple transfections of different amounts of shRNA expression vectors No. 40 and No. 50. The control transfection contains the HBV replicon only, with no test plasmid, and provides a measure of sAg secretion in the absence of the No. 40 and No. 50 vectors. A simple "percent inhibition" calculation is done by taking the ratio of sAg expression in the presence of test plasmid and the level of sAg expression in control (HBV replicon-only) transfections. By further mathematical transformation and graphical representation of the data, it was possible to construct dose-response inhibition curves and calculate an IC50 value (the concentration of vector at which 50% of surface antigen secretion is inhibited), which in turn allows for a standardized means of comparison of the effectiveness of various test vectors in multiple experiments. The curves, data transformations and IC50 values were generated using EnzFitter software (Biosoft, Ferguson, Mo., USA).

The results of these experiments are shown in FIGS. 6 and 7. Notably, close to 100% inhibition of sAg expression is achieved at moderate doses of test vector (25 ng). Furthermore, a very small dose, 1 ng, is sufficient to reduce sAg expression significantly (about 30 to 40 percent). A more detailed analysis of the dose response to these plasmids is given in FIG. 7, where it is evident that saturation of the inhibitory effect is achieved at moderate doses of test vectors, and an IC50 value (the concentration of vector at which 50% of the inhibition is achieved) is approximately 5 ng.

Example 2

A Four-Promoter RNA Polymerase III-Based Expression Construct for Production of shRNAs which Reduce Hepatitis B RNA Production and Replication FIG. 9 is a diagram of vector pHB4 which contains 4 polymerase III promoter-shRNA cassettes. The labeling of the figure indicates the promoter name, the associated shRNA (targeting the HBV genome) and the direction of transcription for each cassette. The vector was constructed as described above using an iterative process of adding shRNA cassettes stepwise. The data in FIG. 10 (a luciferase assay essentially similar to that used in Example 1) indicate that all 4 promoter/shRNA cassettes were active in silencing their target sequences in a cell supplied with the vector and an assayable substrate (luciferase fusion constructs as in Example 1, now including the shRNA-799 construct). The Table in FIG. 10 shows triplicate independent experiments for pHB4 and as positive controls, results from the single hairpin vectors are given as well. The data in FIG. 12 show that the same construct was able to silence HBV gene expression in a cell transfected with the test vector and an HBV replicon, in IC50 determinations as explained in Example 1. FIG. 12 summarizes results from experiments where the potency and activity of a series of vectors (from 1 to 4 shRNA as indicated in FIG. 8) were evaluated at various input concentrations of plasmid to replicate cell cultures. First, the production of HBV antigens (either surface antigen "sAg" or "e" antigen "eAg") were measured by an ELISA immunoassay in the cells receiving only the HBV replicon. At each of several test input amounts (concentrations) of vector, the amount of ELISA antigen produced is compared to the level produced with no test vector. The concentration of vector at which the antigen produced is reduced 50% relative to the cells not supplied with the vector is defined as the IC50 (inhibitory concentration to achieve 50% inhibition). The lower the IC50 value the more potent is the agent or drug. The figure shows that the IC50 value decreased substantially when increasing from 1 promoter/shRNA cassette vector to the pHB4 example containing 4 promoter/shRNA cassettes. It should be noted that the IC50 values may have also been affected by the relative potency and transcription levels of each shRNA molecule, and did not reflect a simple relationship to the concentration of the vector only, which in effect behaved as four drugs after entering the cell and expressing the four encoded dsRNA molecules. In other words, the increased potency reflects not only the greater number of total shRNA transcripts generated by the vector, but the also the individual potency that each shRNA has to effect the reduction of sAg or eAg production via degradation of the target viral RNA molecules. Taking the FIG. 12 IC50 data together with the luciferase reporter data in FIG. 10, it is apparent that the progressive addition of shRNA cassettes increased the potency of the vector in an apparently quantitative manner, and furthermore increased the pharmacological activity against the HBV target by inhibiting four distinct sites of the HBV target. It is important to recognize, however, that the ability of the multiple polymerase III expression constructs of the invention to express multiple individual antiviral dsRNA hairpin molecules is of significant value in and of itself, not just because of associated increases in "potency". Where the level of antiviral efficacy is high, the incremental quantitative increase in viral inhibition seen with each additional dsRNA molecule may be less important per se than the ability of the constructs of the invention to deliver what is in effect a multi-drug regimen, with the inherent advantage of being highly resistant to the development of viral resistance.

Example 3

A Multiple RNA Polymerase III Promoter Vector in which a Single Promoter Expresses a 2-Hairpin (Bi-Finger) Containing Short RNA In another embodiment of this invention comprising multiple Pol III promoter vectors, it is possible to express more than one shRNA effector molecule from a single promoter, thus increasing the number of RNA sequences it is possible to target with a greater economy of promoter elements. For example, the invention can be used to express 3 shRNA molecules using only 2 Pol III promoters; 4, 5, or 6 shRNA molecules using only 3 pol III promoters; 5, 6, 7, or 8 shRNA molecules using 4 pol III promoters, etc. The expression of a "double-hairpin" or bi-fingered dsRNA was demonstrated here by creating a U6 promoter vector in which two of the HBV targeting shRNA-encoding sequences (FIG. 5) were connected by short spacer elements to produce one longer RNA molecule (total lengths of approximately 140 nucleotides using the long spacer, approximately 60 bases using the short spacer) containing two active shRNA elements, in this case comprising the 1737 and the 2791 sequences. The luciferase fusion targets as described in Example 1 were used in this experiment and the results are shown in the bottom panel of FIG. 13. Both forms of the double-hairpin constructs were effective in mediating the significant degradation of both target sequences in the luciferase fusion assay. The role of the space sequence in these constructs is ostensibly to separate the hairpin-forming sequences into two distinct domains and to facilitate cleavage by single-strand endonucleases. Those skilled in the art will recognize that a number of variant lengths and sequences of the spacer will allow the appropriate double-hairpin structure to form and effect dual target sequence degradation. However, it will also be appreciated that spacer sequences of a length and composition capable of themselves forming secondary structures or of base pairing with sequences of the flanking shRNA would likely interfere with the function of the dual hairpin molecule.

Example 4

DNA Vectors Combined with Pharmaceutical Formulations Mediate Uptake and Gene Expression in the Mouse Liver An important indication that the multiple promoter inventions disclosed herein for silencing HBV gene expression are suitable as pharmaceutical agents was demonstrated by their injection directly into the bloodstream of a mouse together with a DNA vector that generated HBV surface antigen RNA and protein. In these experiments, the pHB4 vector (see FIG. 9) was delivered to mice by hydrodynamic tail vein injection together with an sAg plasmid that expressed the HBV surface antigen specifically in the liver (this plasmid expresses the sAg under control of the albumin promoter and was derived from plasmid pAlb-hGH as described by Chisari et al., *J. Virol.* 60:880-87 (1986)). Hydrodynamic tail vein injection is commonly used by those skilled in the art to rapidly perfuse liver tissue with an exogenous agent in the living animal. Since sAg is secreted by the liver cells in this model, it was measured in the serum of the mice four days after the injection of DNA. A third vector, expressing luciferase under the CMV promoter, was coinjected to enable normalization of sAg values to liver luciferase, and thereby control for total DNA uptake and expression of DNA in the liver. The results of this experiment are indicated in FIG. 14. Two sets of mice were used for the co-injections and yielded values of serum sAg of 0.07 and 0.08 OD units respectively. Since introduction of the sAg expression vector alone, without the shRNA pHB4 vector, yielded an average value of 0.47 OD units, it is evident that silencing of sAg was accomplished dramatically in vivo with pHB4.

Example 5

Alteration of the 7SK Promoter/shRNA Junction Sequence Substantially Increases Potency of shRNA Expression Vector While it has been reported that the human 7SK promoter is primarily dependent upon "upstream" sequences (those 5' of the start site of transcription) for its function, nucleotide sequences located downstream of the transcription start site may also modulate the function of the promoter (see Sandrock and Benecke, Gene Expr. 8:105-14 (1999) and Koper-Emde et al., Biol. Chem. 385:791-94 (2004). Applicants have previously observed that dsRNA hairpin molecules targeting a sequence for gene silencing frequently remain functional even if several additional nucleotides not corresponding to the target sequence are interposed between the RNA polymerase III transcriptional start site and the beginning of the target sequence. This allows for the maintenance of improved function of Pol III promoter/shRNA cassettes wherein restriction sites or spacer elements are added. Applicants have created a novel 7SK promoter element (FIG. 4e) which utilizes the first 234 bases of the native promoter, then followed by 10 synthetic bases comprising a Sal I restriction site recognition sequence (or an alternative six nucleotides, desirably comprising a restriction site recognition sequence) and 4 A residues. This novel promoter sequence element is designated 7SK4a and essentially inserts the sequence GTCGACAAAA (SEQ ID NO: 12) to be transcribed and therefore appended to the 5' end of the shRNA molecules represented in FIG. 5. As shown in FIG. 11, three shRNA sequences (1737, 1943, and 799) were tested for their silencing effects on HBV antigen expression in three different promoter contexts: the U6 promoter (FIG. 4c), the 7SK promoter (FIG. 4a) and the 7SK4a promoter (FIG. 4e). The potency of the 9 constructs was evaluated by IC50 determination for sAg and eAg as described in the previous examples. With all 3 shRNA sequences tested, the 7SK4a configuration gave significantly lower IC50 values than the other two promoters.

---

We claim:

1. An expression construct comprising at least two different RNA polymerase III promoters, wherein each promoter is operably linked to a nucleic acid sequence encoding at least one RNA effector molecule, wherein at least one of said RNA polymerase III promoters comprises SEQ ID NO:5.

2. The expression construct of claim 1, wherein the at least, two different RNA polymerase III promoters are of viral or eukaryotic origin.

3. The expression construct of claim 1, wherein the at least two different RNA polymerase III promoters are independently selected from type 1 RNA polymerase III promoters, type 2 RNA polymerase III promoters, and type 3 RNA polymerase III promoters, wherein said type 3 RNA polymerase III promoters include H1, 7SK, U6, and MRP.

4. The expression construct of claim 1, wherein said at least one RNA effector molecule is a short hairpin RNA.

5. The expression construct of claim 4, wherein said short hairpin RNA comprises a nucleic acid sequence selected from SEQ ID NO:6, SEQ ID NO:7, SEQ ID NO:8, SEQ ID NO:9, SEQ ID NO:10, and SEQ ID NO:11; wherein U is substituted for T.

6. The expression construct of claim 1, wherein said expression construct comprises three to eight RNA polymerase III promoters.

7. The expression construct of claim 6, wherein said expression construct comprises four RNA polymerase III promoters.

8. The expression construct of claim 7, comprising a 7SK and a U6 promoter.

9. The expression construct of claim 6, wherein the RNA polymerase III promoters are selected from H1, 7SK, and U6.

10. The expression construct of claim 1, wherein said at least one RNA effector molecule is capable of modulating the expression of a target gene.

11. The expression construct of claim 10, wherein said target gene is a viral gene.

12. The expression construct of claim 11, wherein said viral gene is an HBV, HCV, HIV, HPV, influenza, or West Nile virus gene.

13. The expression construct of claim 1, wherein at least two of said RNA polymerase III promoters are operably linked to sequences encoding different RNA effector molecules.

14. The expression construct of claim 1, wherein each RNA polymerase III promoter is operably linked to a nucleic acid sequence encoding the same RNA effector molecule.

15. The expression construct of claim 1, wherein no more than two copies of the same RNA polymerase III promoter is present.

16. The expression construct of claim 15, wherein no more than one copy of the same RNA polymerase III promoter is present.

17. the expression construct of claim 1, wherein the SEQ ID NO:5 nucleotides 241 to 244 comprise gggg.

18. An expression construct comprising two or more RNA polymerase III promoters, wherein at least two of said RNA polymerase III promoters are operably linked to a nucleic acid sequence encoding a short hairpin RNA molecule, wherein at least one of said RNA polymerase III promoters comprises SEQ ID NO:5.

19. The expression construct of claim 18, wherein at least two of said RNA polymerase III promoters are operably linked to nucleic acid sequences encoding the same short hairpin RNA molecule.

20. The expression construct of claim 18, wherein at least two of said RNA polymerase III promoters are operably linked to sequences encoding different short hairpin RNA molecules.

21. The expression construct of claim 18 wherein at least two of said RNA polymerase III promoters are the same RNA polymerase III promoter.

22. The expression construct of claim 18 wherein said two or more RNA polymerase III promoters include at least two different RNA polymerase III promoters.

23. The expression construct of claim 18, wherein said two or more RNA polymerase III promoters comprise type 3 RNA polymerase III promoters.

24. The expression construct of claim 18, wherein at least one of said RNA polymerase III promoters is operably linked to a sequence encoding a short hairpin RNA molecule which is a bi-finger or multi-finger dsRNA hairpin.

25. The expression construct of claim 18, wherein the RNA polymerase III promoters are selected from H1, 7SK, and U6.

26. The expression construct of claim 18 which is capable of modulating the expression of a target gene.

27. The expression construct of claim 26, wherein said target gene is a viral gene.

28. The expression construct of claim 27, wherein said viral gene is an HBV, HCV, HIV, HPV, or West Nile Virus gene.

29. A pharmaceutical composition comprising the expression construct of claim 1.

30. An expression vector comprising at least two different RNA polymerase III promoters, wherein each of said RNA polymerase III promoters is suitable for expression of a small RNA molecule, wherein at least one of said RNA polymerase III promoters comprises SEQ ID NO:5.

31. The expression vector of claim 30, wherein the at least, two different RNA polymerase III promoters are independently selected from a type 1 RNA polymerase III promoter, a type II RNA polymerase III promoter, and a type 3 RNA polymerase III promoter, 32. The expression vector of claim 30, wherein the at least two different RNA polymerase III promoters are each selected from H1, 7SK, U6, and MRP.

33. The expression vector of claim 30, wherein the expression vector has from three to eight RNA polymerase III promoters.

34. The expression vector of claim 33, wherein the expression vector has four RNA polymerase III promoters.

35. The expression vector of claim 33, wherein the RNA polymerase III promoters are selected from H1, 7SK, and U6.

36. The expression vector of claim 34, wherein the at least two different RNA polymerase III promoters include a 7SK promoter and a U6 promoter.

37. The expression vector of claim 30, wherein at least one RNA polymerase III promoter has the nucleotide sequence of SEQ ID NO: 5.

38. The expression vector of claim 30, wherein the nucleotides 241 to 244 of SEQ ID NO: 5 are gggg.

39. The expression vector of claim 32, wherein the vector contains a 7SK promoter, and the 7SK promoter comprises nucleotides 1-234 of SEQ ID NO: 1.

40. The expression vector of claim 32, wherein the vector contains an H1 promoter, and the H1 promoter comprises nucleotides 1-125 of SEQ ID NO: 2.

41. The expression vector of claim 32, wherein the vector contains a U6 promoter, and the U6 promoter comprises nucleotides 1-264 of SEQ ID NO: 3.

42. The expression vector of claim 32, wherein the vector contains a 7SK promoter, and the 7SK promoter comprises nucleotides 1-244 of SEQ ID NO: 4.

43. The expression vector of claim 33, wherein at least two RNA polymerase III promoters are the same.

44. The expression vector of claim 30, wherein the vector is a plasmid.

45. The expression vector of claim 44, wherein the plasmid has a pUC backbone.

46. The expression vector of claim 30, wherein the vector contains restriction sites for insertion of DNA expression cassettes, such that transcription of each of said DNA expression cassettes is controlled by one of said RNA polymerase III promoters.

47. The expression vector of claim 30, wherein the vector contains an oligo(dT) termination signal operably linked to each RNA polymerase III promoter.

48. The expression vector of claim 30, wherein the vector further comprises a bacterial origin of replication and a bacterial antibiotic resistance gene.

49. The expression vector of claim 48, wherein the antibiotic resistant gene is a kanamycin resistance gene.

50. The expression vector of claim 36, wherein the U6 and 7SK promoters are positioned to direct transcription from adjacent expression cassettes.

51. The expression vector of claim 50, wherein the U6 and 7SK promoters are positioned to direct, transcription in the same direction.

52. The expression vector of claim 50, wherein the U6 and 7SK promoters are positioned to direct transcription in opposite directions.

53. The expression vector of claim 50, wherein the vector has a second U6 promoter positioned at a distal location from said U6 and 7SK promoters.

54. The expression vector of claim 35, wherein the vector comprises a 7SK promoter and an H1 promoter positioned to direct transcription from adjacent expression cassettes.

55. The expression vector of claim 54, wherein the 7SK and H1 promoters are positioned to direct transcription in the same direction.

56. The expression vector of claim 54, wherein the 7SK and H1 promoters are positioned to direct transcription in opposite directions.

57. The expression vector of claim 54, having a U6 promoter positioned at a distal location from said 7SK and H1 promoters.

58. The expression vector of claim 34, wherein the vector has a first 7SK promoter and a second 7SK promoter positioned to direct transcription from adjacent expression cassettes, and in the same direction.

59. The expression vector of claim 58, wherein a third 7SK promoter and a U6 promoter are positioned to direct transcription from adjacent expression cassettes, and in the same direction.

60. The expression vector of claim 59, wherein the first and second 7SK promoters are separated from said third 7SK promoter and said U6 promoter by an antibiotic resistance gene.

61. The expression vector of claim 60, wherein the antibiotic resistance gene is a kanamycin resistance gene.

62. A pharmaceutical composition comprising the expression construct of claim 18.

* * * * *